US008778400B2

(12) United States Patent
Prestidge et al.

(10) Patent No.: US 8,778,400 B2
(45) Date of Patent: Jul. 15, 2014

(54) NANOPARTICLE-STABILIZED CAPSULE FORMULATION FOR TREATMENT OF INFLAMMATION

(75) Inventors: Clive Allan Prestidge, Semaphore South (AU); Spomenka Simovic, Adelaide (AU)

(73) Assignee: University of South Australia, Adelaide, South Australia (AU)

( * ) Notice: Subject to any disclaimer, the term of this patent is extended or adjusted under 35 U.S.C. 154(b) by 811 days.

(21) Appl. No.: 12/426,530

(22) Filed: Apr. 20, 2009

(65) Prior Publication Data

US 2009/0263486 A1 Oct. 22, 2009

Related U.S. Application Data

(60) Provisional application No. 61/046,539, filed on Apr. 21, 2008.

(51) Int. Cl.
| | |
|---|---|
| A61K 9/14 | (2006.01) |
| A61K 31/415 | (2006.01) |
| A61K 31/405 | (2006.01) |
| A61K 9/50 | (2006.01) |
| A61K 9/51 | (2006.01) |
| A61K 31/18 | (2006.01) |
| A61K 31/685 | (2006.01) |
| A61K 47/14 | (2006.01) |
| A61K 47/44 | (2006.01) |
| A61K 31/695 | (2006.01) |

(52) U.S. Cl.
CPC .............. *A61K 9/501* (2013.01); *A61K 9/5089* (2013.01); *A61K 9/5115* (2013.01); *A61K 9/5192* (2013.01); *A61K 31/405* (2013.01); *A61K 31/18* (2013.01); *A61K 31/685* (2013.01); *A61K 47/14* (2013.01); *A61K 47/44* (2013.01); *A61K 31/695* (2013.01)

USPC ........................... 424/489; 514/420; 514/406

(58) Field of Classification Search
CPC . A61K 9/5089; A61K 9/5115; A61K 9/5192; A61K 9/501
USPC ........................... 424/400, 489; 514/420, 406
See application file for complete search history.

(56) References Cited

U.S. PATENT DOCUMENTS

| | | | |
|---|---|---|---|
| 3,850,655 | A | 11/1974 | Adams |
| 5,185,155 | A | 2/1993 | Behan et al. |

(Continued)

FOREIGN PATENT DOCUMENTS

| | | |
|---|---|---|
| EP | 0478326 B1 | 4/1992 |
| WO | 0247665 A2 | 6/2002 |

(Continued)

OTHER PUBLICATIONS

Miglyol, Sasol Germany GmbH [Downloaded Jul. 2, 2011] [Retrieved from internet <URL: http://abstracts.aapspharmaceutica.com/expoaaps07/Data/EC/Event/Exhibitors/236/cb63fb76-28f4-4948-a6d0-ae249dae9c30.pdf >], 1 page.*

(Continued)

*Primary Examiner* — Jason Sims
*Assistant Examiner* — Miriam A Levin
(74) *Attorney, Agent, or Firm* — Rothwell, Figg, Ernst & Manbeck, P.C.

(57) ABSTRACT

A formulation for the delivery of an anti-inflammatory agent to a subject is described. In one particular application of the invention, the formulation comprises oil-based or aqueous droplets comprising indomethacin (1-(4-chlorobenzoyl)-5-methoxy-2-methyl-1-H-indole-3-acetic acid) or celecoxib (4-[5-(4-methylphenyl)-3-(trifluoromethyl) pyrazol-1-yl] benzenesulfonamide) stabilized by nanoparticles, particularly silica nanoparticles.

40 Claims, 10 Drawing Sheets

(56) References Cited

U.S. PATENT DOCUMENTS

| | | | |
|---|---|---|---|
| 5,500,223 A | 3/1996 | Behan et al. | |
| 5,670,139 A | 9/1997 | Allard et al. | |
| 5,843,509 A * | 12/1998 | Calvo Salve et al. | 424/489 |
| 5,876,755 A | 3/1999 | Perring et al. | |
| 5,993,846 A * | 11/1999 | Friedman et al. | 424/434 |
| 6,391,321 B1 | 5/2002 | Gers-Barlag et al. | |
| 6,413,548 B1 * | 7/2002 | Hamer et al. | 424/489 |
| 6,585,983 B1 | 7/2003 | Gers-Barlag et al. | |
| 2002/0028238 A1 * | 3/2002 | Karim et al. | 424/461 |
| 2003/0175317 A1 | 9/2003 | Barthel et al. | |
| 2004/0001891 A1 | 1/2004 | Smith et al. | |
| 2004/0072784 A1 * | 4/2004 | Sant et al. | 514/44 |
| 2004/0202682 A1 | 10/2004 | Emrick et al. | |
| 2005/0006800 A1 | 1/2005 | Mountziaris et al. | |
| 2006/0083781 A1 | 4/2006 | Shastri et al. | |
| 2006/0115495 A1 * | 6/2006 | Yacaman et al. | 424/204.1 |
| 2008/0193513 A1 | 8/2008 | Prestidge et al. | |
| 2009/0181076 A1 | 7/2009 | Prestidge et al. | |
| 2010/0136124 A1 | 6/2010 | Prestidge et al. | |

FOREIGN PATENT DOCUMENTS

| | | | | |
|---|---|---|---|---|
| WO | WO 0247665 A2 * | 6/2002 | | A61K 9/50 |
| WO | 03082232 A1 | 10/2003 | | |
| WO | 2006130904 A1 | 12/2006 | | |
| WO | 2006133518 A1 | 12/2006 | | |
| WO | WO 2006130904 A1 * | 12/2006 | | A61K 9/50 |
| WO | WO 2006133518 A1 * | 12/2006 | | A61K 9/66 |
| WO | 2007128066 A1 | 11/2007 | | |
| WO | WO 2007128066 A1 * | 11/2007 | | A61K 9/107 |

OTHER PUBLICATIONS

Mason et al., Topical NSAIDs for acute pain: a meta-analysis, BMC Family Practice 2004, 5:10 doi 10.1186/1471-2296-5-10 [Downloaded Jul. 2, 2011] [Retrieved from internet <URL: http;//www.biomedcentral.com/1471-2296/5/10 >], 15 pages.*

Simovic et al., Dry Hybrid Lipid-Silica Microcapsules Engineered from Submicron Lipid Droplets and Nanoparticles as a Novel Delivery System for Poorly Soluble Drugs, Molecular Pharmaceutics (ACS, published on web Apr. 9, 2009) 6(3):861-872.*

Beck et a. (Nanoparticle-coated microparticles: preparation and characterization, J. Microencapsulation (Aug. 2004), vol. 21, No. 5, pp. 499-512 (15 pages).*

Bos, J.D., et al., "The 500 Dalton rule for the skin penetration of chemical compounds and drugs," Exp. Dermatol., 9:165-169 (2000).

Brown, M.B., et al., "Dermal and Transdermal Drug Delivery Systems: Current and Future Prospects," Drug Delivery, 13(30): 175-187 (2006).

Christensen, K.L., et al., "Preparation of Redispersible Dry Emulsions by Spray Drying," International Journal of Pharmaceutics, 212: 187-194 (2001).

Jennings, V., et al., "Vitamin A loaded solid lipid nonoparticles for topical use: occulusive properties and drug targeting to the upper skin," European Journal of Pharmaceutics and Biopharmaceutics, 49(3): 211-218 (2000).

Weete, J.D., et al., "Improvement of Lecithin as an Emulsifier for Water-in-Oil Emulsions by Thermalization," JAOCS, 71(7): 731-737 (Jul. 1994).

Derwent On-line Abstract Accession No. 2004-611106/200659 (2004) of KR 3091539A, published Dec. 3, 2003.

Daniels, Rolf, scf-online.com, Issue 25, Daniels: Galenic principles of modern skin care products, Skin Care forum, Issue 25, Apr. 2001 (online) <URL:http://222.scf-online.com/english/25_e/galenic_25_e.htm>.

Hsu, Ming F., "Charged Colloidal Particles in Nonpolar Solvents and Self-assembled Colloidal Model Systems," A thesis presented to the Department of Physics, Harvard University, Cambridge, Massachusets, Sep. 2004, 111 pages.

Hwang, Yi-Jeong, "Controlled release of retinol from silica particles prepared in O/W/O emulsion: The effects of surfactants and polymers," Journal of Controlled Release, 106: 339-349 (2005).

Noble, P.F. et al., "Fabrication of 'Hairy' Colloidosomes with Shells of Polymeric Microrods," J. Am. Chem. Soc. Communications, 126: 8092-8093 (2004).

Prestidge, Clive A., "Polymer and particle adsorption at the PDMS droplet-water interface," Advances in Colloid and Interface Science, 108-109: 105-118 (2004).

Prestidge, C.A., et al., Poster titled "Nanoparticle coated droplets: a platform delivery system for lipophlic drugs," Pharmaceutical Sciences World Congress, Amsterdam, The Netherlands, Apr. 22-25, 2007.

Rowe, R.C., et al. (eds.), Handbook of Pharmaceutical Excipients, Fifth Edition, Pharmaceutical Press, 6 pages (2005).

Simovic, Spomenka, et al., "Hydrophilic Silica Nanoparticles at the PDMS Droplet-Water Interface," Langmuir, 19: 3785-3792 (2003).

Simovic, Spomenka, et al., "Adsorption of Hydrophobic Silica Nanoparticles at the PDMS Droplet-Water Interface," Langmuir, 19:20, 8364-8370 (2003).

Simovic, Spomenka, et al., "Nanoparticles of Varying Hydrophobicitiy at the Emulsion Droplet-Water Interface: Adsorption and Coalescence Stability," Langmuir, 20:8357-8365 (2004).

Tan, A., et al., Poster titled Nanoparticle Encapsulated Droplets: A Novel Delivery System for Lipophilic Drugs, 34th Annual Meeting & Exposition of the Controlled Release Society, Long Beach Convention Center, Long Beach, California, USA, Jul. 7-11, 2007.

Wang, Dayang, "The water/oil interface: the emerging horizon for self-assembly of nanoparticles," Soft Matter, 1:6, 412-416 (2005).

Zhang, Liangfang, et al., "How to Stabilize Phospholipid Liposomes (Using Nanoparticles)," Nano Letters, 6:4, 694-698 (2006).

Dinsmore, A.D., "Colloidosomes: Selectively Permeable Capsules Composed of Colloidal Particles," Science, 298: 1006-1009 (Nov. 1, 2002).

Tan et al. "Siiica-Lipid Hybrid (SLH) Versus Non-lipid Formulations for Optimising the Dose-Dependent Oral Absorption of Celecoxib" Pharm., Res. 28:2273-2287, 2011.

Nguyen et al. "Silica-lipid hybrid (SLH) formulations enhance the oral bioavailability and efficacy of celecoxib: An in vivo evaluation" J. Cont. Rel. 167:85-91, 2013.

* cited by examiner

A

B

A

B

A

B

A

B

NANOPARTICLE-STABILIZED CAPSULE FORMULATION FOR TREATMENT OF INFLAMMATION

INCORPORATION BY REFERENCE

This patent application claims priority from:

U.S. 61/046,539 titled "Nanoparticle-coated capsule formulation for treatment of inflammation" filed on 21 Apr. 2008.

The entire content of this application is hereby incorporated by reference.

The following International patent applications are referred to herein:

PCT/AU2006/000771 (WO 2006/130904) titled "Dried formulations of Nanoparticle-coated capsules", and PCT/AU2007/000602 (WO 2007/128066) titled "Drug release from nanoparticle-coated capsules".

The entire content of each of these applications is hereby incorporated by reference.

FIELD OF THE INVENTION

The present invention relates to a formulation for the delivery of an anti-inflammatory agent to a subject. In a particular application of the invention, the formulation comprises oil-based or aqueous droplets comprising indomethacin (1-(4-chlorobenzoyl)-5-methoxy-2-methyl-1-H-indole-3-acetic acid) or celecoxib (4-[5-(4-methylphenyl)-3-(trifluoromethyl) pyrazol-1-yl]benzenesulfonamide) within a coating of nanoparticles, particularly silica nanoparticles.

BACKGROUND OF THE INVENTION

Celecoxib is a non-steroidal anti-inflammatory drug (NSAID) used in the treatment of osteoarthritis, rheumatoid arthritis, acute pain, painful menstruation and menstrual symptoms and to reduce the number of colon and rectum polyps in subjects with familial adenomatous polyposis. It has additionally been demonstrated that celecoxib may reduce the incidence of certain cancers such as colon cancer, ultraviolet B radiation-induced skin cancer, oral cancer (Sood et al., 2005) and breast cancer (Kawamori et al., 1998; Fischer et al., 1999; and Harris et al., 2000).

Celecoxib functions by specifically inhibiting the enzyme cyclooxygenase-2 (COX-2). There are two forms of COX, namely COX-1 and COX-2, and both enzymes bring about the conversion of arachidonic acid to prostaglandin (PG), a local mediator involved in the generation of biological responses such as pain, fever and inflammatory symptoms. However, COX-2 expression is induced under inflammatory conditions, whereas COX-1 is constitutively expressed in healthy tissues in physiological (normal) processes (Kujubu et al., 1991; Masferrer et al., 1992; Siebert et al., 1994; and Xie et al., 1991). In contrast to specific COX-2 inhibitors such as celecoxib, conventional NSAIDs non-selectively inhibit both COX-1 and COX-2. Inhibiting physiological (COX-1 mediated) production of prostaglandins inhibits gastroduodenal mucosal defence, the renal system and platelet aggregation (Fischer et al., 1999; Fulton, 1984; Narisawa et al., 1983; Pentland et al., 1999; and Reddy et al., 1993), and long term use of such conventional NSAIDs is accordingly associated with significant side effects.

When delivered orally to achieve systemic therapy, celecoxib can be used to treat the symptoms of pain and inflammation without side-effects on the gastric tract, renal system or platelets, symptoms that are associated with conventional NSAIDs. It can alternatively be delivered topically for treatment of osteoarthritis, rheumatoid arthritis, and the treatment and prevention of colorectal and oral cancers, amongst other conditions.

However, celecoxib is considered difficult to formulate because of its chemical properties. It exists in three polymorphic forms, is weakly acidic, hydrophobic (log P≈3.5), and classified as having low solubility (7 µg/ml) and, accordingly, has low bioavailability. It does, however, have a high "Tmax" (that is, the time necessary to achieve maximal drug concentration in circulation) of approximately three hours after oral delivery. This means that the material that is bioavailable is well absorbed by the gut and readily enters into circulation; however, as the bioavailability is low, absorption is incomplete and variable. Further, this is considered to be a slow onset of action for pain relief. Celecoxib is also considered difficult to process into solid dosage forms.

Various systems have been developed to improve solubility of active substances, such as celecoxib, that are difficult to formulate. Some of these systems are also capable of mediating the effective delivery of active substances to target areas. An example of such a system is an encapsulated emulsion.

Emulsions are dispersed systems consisting of two immiscible liquids, one of which is dispersed (the dispersed or discontinuous phase) in a continuous phase, as droplets. If the droplets are oil-based droplets, then the emulsion can solubilise or complex amphiphilic or lipophilic active substances, whereas, if the droplets are aqueous, then water-soluble active substances can be entrapped. The dispersed droplets may comprise or include a suitably soluble substance, for example an active substance such as a drug compound; the dispersed droplets thereby acting as delivery vehicles.

To improve droplet stability in pharmaceutical applications, where the vehicles are used under physiological conditions, droplets can be encapsulated with a protective coating, producing encapsulated droplets known as capsules. The present invention is directed to the provision of capsules of this kind that are particularly well suited to use with celecoxib and like compounds, show good levels of droplet stability in physiological conditions and over time (ie in storage), appear to enhance the delivery of the active substance (ie relative to Celebrex® formulation, a currently marketed formulation of celecoxib), and which may, in turn, enhance the bioavailability of the active substance.

SUMMARY OF THE INVENTION

In a first aspect, the present invention provides a nanoparticle-stabilised capsule formulation comprising an active substance selected from the group consisting of anti-inflammatory agents, preferably NSAID agents, wherein said formulation comprises droplets of a suitable carrier comprising said active substance and, optionally, an emulsifier, wherein said droplets are stabilised with nanoparticles coated on the surface of the droplets and, optionally, dispersed within said carrier.

Preferably, the said droplets are coated with at least one layer of nanoparticles.

The active anti-inflammatory substance may be selected from the group consisting of non-specific inhibitors of COX-1 and COX-2 and/or the group consisting of specific inhibitors of COX-2.

The formulation is preferably formulated for oral (p.o.) administration to a subject. Alternatively, the formulation may be formulated for topical application to the skin for transdermal or dermal administration of the active substance, or mucosal application.

The formulation may release the active substance in a controlled manner, for example, in a sustained manner or, otherwise, such that the active substance is rapidly released upon administration.

In a second aspect, the present invention provides a dried nanoparticle-stabilised capsule formulation comprising an active substance selected from the group consisting of anti-inflammatory agents, said formulation comprising capsules comprising a porous matrix of said active substance, a suitable carrier, nanoparticles and, optionally, an emulsifier, and wherein said capsules are dispersable into droplets of said carrier, comprising the active substance, that are stabilised with nanoparticles coated on the surface of the droplets and, optionally, dispersed within said carrier.

In a third aspect, the present invention provides a method for administering an active substance selected from the group consisting of anti-inflammatory agents, preferably NSAID agents, wherein said method comprises administering to said subject a formulation according to the first or second aspect.

Preferably, the subject is suffering from pain and/or inflammation, or cancer.

In a fourth aspect, the present invention provides a method for producing a formulation of an active substance selected from the group consisting of anti-inflammatory agents, preferably NSAID agents, wherein said method comprises preparing a nanoparticle-stabilised preparation comprising droplets of a suitable carrier comprising said active substance and, optionally, an emulsifier, wherein said droplets are stabilised with nanoparticles coated on the surface of the droplets and, optionally, dispersed within said carrier.

In a fifth aspect, the present invention provides a method for enhancing the bioavailability of an active substance selected from the group consisting of anti-inflammatory agents, preferably NSAID agents, wherein said method comprises preparing a nanoparticle-stabilised preparation comprising droplets of a suitable carrier comprising said active substance and, optionally, an emulsifier, wherein said droplets are stabilised with nanoparticles coated on the surface of the droplets and, optionally, dispersed within said carrier.

DETAILED DESCRIPTION OF THE INVENTION

Figure 1:
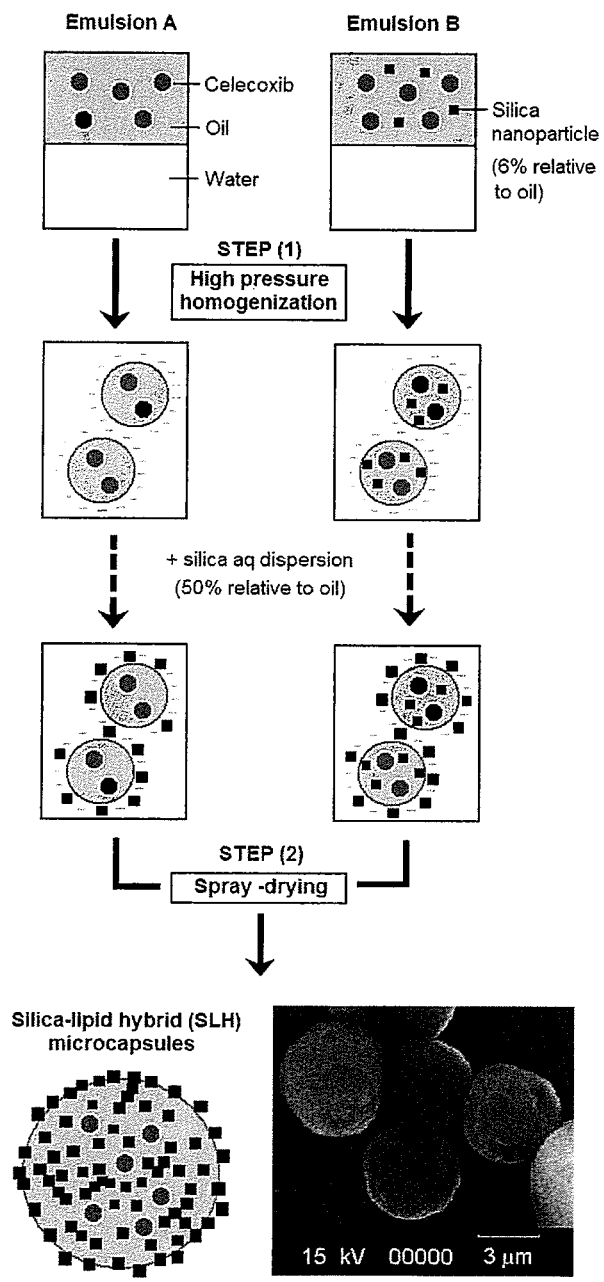
FIG. 1 provides (a) a schematic representation of capsule formation and scanning electron micrograph (SEM) of the capsules, and (b) SEM of the cross-section of a capsule showing the stabilised porous matrix of a dried formulation.
Figure 1:
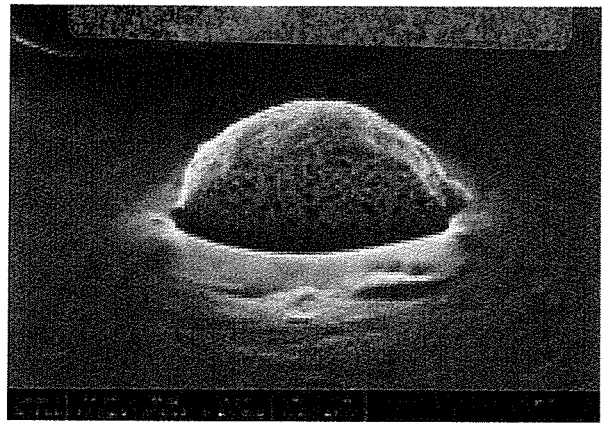

The present invention is particularly directed to the provision of a formulation comprising nanoparticle-stabilised capsules containing celecoxib or a like compound, however it is considered that the formulation may be usefully applied to other anti-inflammatory agents such as, in particular, indomethacin. The formulation may show enhanced bioavailability relative to existing formulations of indomethacin, celecoxib and like compounds, which may, in turn, allow for more effective therapeutic use.

Thus, in a first aspect, the present invention provides a nanoparticle-stabilised capsule formulation comprising an active substance selected from the group consisting of anti-inflammatory agents, preferably NSAID agents, wherein said formulation comprises droplets of a suitable carrier comprising said active substance and, optionally, an emulsifier, wherein said droplets are stabilised with nanoparticles coated on the surface of the droplets and, optionally, dispersed within said carrier.

Preferably, the said droplets are coated with at least one layer of nanoparticles.

It is to be understood that the term "coated" as used herein may refer to a partial or complete layer or layers of nanoparticles on the surface of the droplets, wherein the nanoparticles are closely or loosely packed. As such, the distribution of nanoparticles coated onto the surfaces of the droplets can be random across the respective droplet surface with varying levels of congregation.

The active anti-inflammatory substance may be selected from the group consisting of non-specific inhibitors of COX-1 and COX-2 and/or the group consisting of specific inhibitors of COX-2.

Particularly preferred examples of non-specific inhibitors of COX-1 and COX-2 include indomethacin, diclofenac (2-(2-(2,6-dichlorophenylamino)phenyl)acetic acid) and naproxen ((+)-(S)-2-(6-methoxynaphthalen-2-yl)propanoic acid).

Particularly preferred examples of COX-2 specific inhibitors include celecoxib, valdecoxib (4-(5-methyl-3-phenyl-isoxazol-4-yl) benzenesulfonamide), meloxicam ((8E)-8-[hydroxy-[(5-methyl-1,3-thiazol-2-yl)amino]methylidene]-9-methyl-10,10-dioxo-10$\lambda^6$-thia-9-azabicyclo[4.4.0]deca-1,3,5-trien-7-one) and rofecoxib (4-(4-methylsulfonylphenyl)-3-phenyl-5H-furan-2-one), and combinations thereof.

However, most preferably, the active substance is indomethacin and/or celecoxib.

The active substance may also be combined with a second active substance (ie for combination therapies), in particular an anti-cancer agent. Presently, celecoxib is being investigated and/or developed for use in combination therapies with anti-cancer agents such as taxotere, docetaxel and temozolomide.

The formulation is preferably formulated for oral (p.o.) administration to a subject. Alternatively, the formulation may be formulated for topical application to the skin for transdermal or dermal administration of the active substance, or mucosal application.

Where the formulation has been formulated for oral administration, the formulation may be in the form of any suitable oral dosage form including tablets, caplets, capsules, liquid emulsions and suspensions and elixirs.

Preferably, the formulation has been spray-dried or is, otherwise, in a dried form. In such a spray-dried or otherwise dried form, the capsules of the formulation may comprise a porous matrix of the active substance, carrier and nanoparticles. A schematic representation of the structure of such a capsule, along with a scanning electron micrograph (SEM) of a cross-section thereof, is shown in FIG. 1. The capsules appear as substantially spheroid structures having a diameter typically in the range of 1 to 5 μm. The average pore size of the pores within the matrix is typically in the range of 25-500 nm. While not wishing to be bound by theory, it is considered that the porous matrix of capsules comprising a spray-dried or otherwise dried formulation of the present invention is a result of the nanoparticles penetrating into the droplets or, alternatively, adsorption of the carrier by the nanoparticles. It has been found, surprisingly, that a formulation according to the present invention, in a spray-dried or otherwise dried form, may be free flowing and exhibit good re-dispersibility (ie may be readily re-dispersed into a liquid to re-form a two-phase liquid system comprising droplets stabilised with nanoparticles coated on the droplet surfaces). It has also been found that the means for drying the formulation may affect its properties; that is, spray-dried formulations, particularly where the carrier is an oil-based or lipidic medium carrier, may exhibit rapid absorption (eg by lipolysis) which may therefore achieve fast therapeutic effects, while similar formulations which have been dried by phase coacervation (filtration), may exhibit slower rates of absorption (eg by lipolysis) which may therefore be better suited for therapies where a sustained therapeutic effect is desired.

The formulation may release the active substance in a controlled manner, for example, in a sustained manner or, otherwise, such that the active substance is rapidly released upon administration.

A formulation according to the present invention may be produced by, for example, any of the suitable methods described in International patent application Nos. PCT/AU2006/000771 (WO 2006/130904) and PCT/AU2007/000602 (WO 2007/128066).

More particularly, a formulation according to the present invention, which upon administration is capable of releasing the active substance in a sustained manner, may be produced by a method comprising the following steps:

(i) dispersing a discontinuous phase comprising a suitable carrier and the active substance into a continuous phase so as to form a two-phase liquid system comprising droplets of said discontinuous phase, each of said droplets having, at its surface, a phase interface; and (ii) allowing nanoparticles provided to said two-phase liquid system to congregate at the phase interface to thereby coat said surface of the droplets in at least one layer of said nanoparticles to form a nanoparticle-stabilised capsule formulation;

wherein said two-phase liquid system is formed, or is otherwise adjusted, so as to have a concentration of a suitable electrolyte which enhances the nanoparticle congregation of step (ii) such that the coating on said surface of the droplets provided by the at least one layer of said nanoparticles, presents a semi-permeable barrier to the active substance.

On the other hand, a formulation according to the present invention, which upon administration is capable of releasing the active substance in a rapid manner, may be produced by a method comprising the following steps:

(i) dispersing a discontinuous phase comprising a suitable carrier and an active substance into a continuous phase so as to form a two-phase liquid system comprising droplets of said discontinuous phase, each of said droplets having, at its surface, a phase interface; and (ii) allowing nanoparticles provided to said two-phase liquid system to congregate at the phase interface to thereby coat said surface of the droplets in at least one layer of said nanoparticles to form a nanoparticle-stabilised capsule formulation;

wherein the active substance is present in the discontinuous phase in an amount greater than its solubility limit in the discontinuous phase.

Preferably, the discontinuous phase is an oil-based or lipidic medium carrier and the continuous phase is aqueous. Suitable oil-based or lipidic medium carriers include triglyceride oils (medium or long-chained), soyabean oil, sunflower oil and almond oil.

The active substance will typically be present in the discontinuous phase at a concentration in the range of 0.01 to 10 wt %, however, it will be well recognised that the actual amount present may vary considerably depending upon, for example, the particular components of the formulation, the solubility of the particular active substance (which can often be increased by the presence of an emulsifier in the discontinuous phase or by otherwise initially providing the nanoparticles in the discontinuous phase) and the manner of release of the active substance that is desired (ie for a rapid release formulation, the active substance may be present in an amount that is greater than its solubility limit in the discontinuous phase, and will therefore preferably be present in an amount that is at least about 100%, more preferably at least about 120%, of the solubility limit of the active substance in the discontinuous phase).

The nanoparticles may be hydrophilic or hydrophobic. In one preferred embodiment, the droplets will be coated with a single layer, or multiple layers, of hydrophilic or hydrophobic nanoparticles. However, in another preferred embodiment, the droplets will be coated with at least two layers of nanoparticles, with the inner layer comprised of hydrophobic nanoparticles and the outer layer comprised of hydrophilic nanoparticles.

Preferably, said nanoparticles have an average diameter of 2-2000 nm, more preferably 5-80 nm, and most preferably about 7 nm. Also, preferably, the size of the nanoparticles will be such that the ratio of nanoparticle size to capsule size (ie the size of the encapsulated droplets) does not exceed 1:15.

Preferably, the nanoparticles are silica nanoparticles, however nanoparticles composed of other substances (eg titania and latex) are also suitable.

Optionally, an emulsifier can be used to stabilise the droplets prior to the congregation of the nanoparticles onto the surfaces of the droplets. Suitable emulsifiers include lecithin, oleylamine, sodium deoxycholate, 1,2-distearyl-sn-glycero-3-phosphatidyl ethanolamine-N, stearylamine and 1,2-dioleoyl-3-trimethylammonium-propane. However, typically any emulsifier that has a HLB (hydrophilic-lipophilic balance) value of less than about 12 can be used. On the other hand, hydrophilic emulsifiers such as sodium dodecyl sulphate (SDS) are less suitable, since these can readily migrate into the continuous phase where they can coat both the droplets and the nanoparticles, when present in high concentrations, thereby preventing nanoparticle congregation.

Preferred emulsifiers are lecithin (which confers a negative charge to the droplets) and oleylamine (which confers a positive charge to the droplets).

The emulsifier will typically be provided in an amount in the range of 0.00001 to 10 wt %, more preferably, in the range of 0.01 to 1 wt %.

Preferably, a formulation according to the present invention includes no other surfactants.

Preferably, a formulation according to the present invention will be produced in the presence of an amount of electrolyte (eg NaCl and/or $KNO_3$) suitable to enhance the congregation of the nanoparticles at the phase interface. The amount of the electrolyte will typically be at least $0.5\times10^{-4}$ M, although a lesser concentration of electrolyte may, however, suffice (eg $1\times10^{-6}$ to $1\times10^{-5}$ M). Preferably, the amount of electrolyte will be at least $1\times10^{-3}$ M, but no more than $1\times10^{-1}$ M.

For a formulation capable of releasing the active substance in a sustained manner, the formulation will preferably be formed from a two-phase liquid system that has been formed, or is otherwise adjusted, so as to have a concentration of a suitable electrolyte which enhances the nanoparticle congregation such that the coating on said surface of the droplets (ie the coating provided by the at least one layer of said nanoparticles), presents a semi-permeable barrier to the active substance. By "semi-permeable barrier", it is to be understood that the coating substantially retards the diffusion of the active substance from within the encapsulated droplets, such that the active substance is released in a controlled manner, in particular, in a sustained manner. Preferably, the semi-permeable barrier presented by the nanoparticle coating retards the diffusion of the active substance from within the encapsulated droplets such that after two hours of being placed in a test medium (eg MilliQ water), at least 25% of the active substance content of the encapsulated droplets has been retained within the encapsulated droplets (ie no more than 75% of the active substance content has been released into the test medium). More preferably, the semi-permeable barrier retards the diffusion of the active substance content of the encapsulated droplets such that at least 35%, and most preferably at least 45%, of the active substance has been retained within the encapsulated droplets after two hours of being placed in a test medium.

Optionally, the encapsulated droplets are provided with a polymer layer around the periphery to modify the interfacial properties of the capsule. Such a polymer layer may comprise cellulose derivatives such as hydroxypropylmethylcellulose and chitosan, or a carbomer, or a mixture thereof.

The discontinuous phase may, optionally, be cross-linked or otherwise further comprise a gelling material so as to form a matrix. Such a matrix may enhance the controlled release (ie sustained release) of the active substance from the encapsulated droplets.

A formulation according to the present invention may be reconstituted from a dried formulation (ie the encapsulated droplets (capsules) of the dried formulation may be re-dispersed into a liquid to re-form a two-phase liquid system). Methods for producing dried nanoparticle-coated capsule formulation are described in International patent application No PCT/AU2006/000771 (WO 2006/130904). Such methods include drying with a rotary evaporator, freeze drying, spray drying, phase coacervation (filtration) or drying using fluidised bed procedures or pressure filtration coupled with vacuum drying.

The formulation may constitute a coacervate of nanoparticle-stabilised capsules.

Thus, in a second aspect, the present invention provides a dried nanoparticle-stabilised capsule formulation comprising an active substance selected from the group consisting of anti-inflammatory agents, said formulation comprising capsules comprising a porous matrix of said active substance, a suitable carrier, nanoparticles and, optionally, an emulsifier, and wherein said capsules are dispersable into droplets of said carrier, comprising the active substance, that are stabilised with nanoparticles coated on the surface of the droplets and, optionally, dispersed within said carrier.

The properties of a formulation according to the present invention, in a spray-dried or otherwise dried form, may be affected by, for example, the inclusion and choice of a particular emulsifier. For example, if an emulsifier that confers a negative charge to the droplets (eg lecithin) is included, the capsules typically comprise a porous matrix (ie of the active substance, carrier, nanoparticles and emulsifier) showing smooth surfaces under SEM with an average pore diameter in the range of 100-500 nm, whereas when an emulsifier that confers a positive charge to the droplets (eg oleylamine) is included, the capsules typically comprise a porous matrix (ie of the active substance, carrier, nanoparticles and emulsifier) showing rough surfaces under SEM (ie structured nanoparticle surface layers are visible) with a higher proportion of 25-100 nm pores.

In a third aspect, the present invention provides a method for administering an active substance selected from the group consisting of anti-inflammatory agents, preferably NSAID agents, wherein said method comprises administering to said subject a formulation according to the first or second aspect.

Preferably, the active anti-inflammatory substance used in the method of the second aspect is selected from the group consisting of non-specific inhibitors of COX-1 and COX-2 and/or specific inhibitors of COX-2.

Preferably, the subject is suffering from pain and/or inflammation. More particularly, the subject may be suffering from osteoarthritis, rheumatoid arthritis, acute pain, painful menstruation or menstrual symptoms, or familial adenomatous polyposis.

Alternatively, the subject is suffering from cancer such as prostate cancer, colon cancer, skin cancer, oral cancer or breast cancer.

In a fourth aspect, the present invention provides a method for producing a formulation of an active substance selected from the group consisting of anti-inflammatory agents, preferably NSAID agents, wherein said method comprises preparing a nanoparticle-stabilised preparation comprising droplets of a suitable carrier comprising said active substance and, optionally, an emulsifier, wherein said droplets are stabilised with nanoparticles coated on the surface of the droplets and, optionally, dispersed within said carrier.

In a fifth aspect, the present invention provides a method for enhancing the bioavailability of an active substance selected from the group consisting of anti-inflammatory agents, preferably NSAID agents, wherein said method comprises preparing a nanoparticle-stabilised preparation comprising droplets of a suitable carrier comprising said active substance and, optionally, an emulsifier, wherein said droplets are stabilised with nanoparticles coated on the surface of the droplets and, optionally, dispersed within said carrier.

Preferably, the method of the fifth aspect is used to enhance the bioavailability of an active anti-inflammatory substance selected from the group consisting of non-specific inhibitors of COX-1 and COX-2 and/or specific inhibitors of COX-2.

The present invention is hereinafter described by way of the following non-limiting examples and accompanying figures.

EXAMPLES

Example 1

Nanoparticle-Stabilised Celecoxib Capsule Formulation

Celecoxib is an active substance of considerable interest to the pharmaceutical industry. Formulating this active substance has, however, been met with difficulties due to its low solubility in aqueous solutions, and correspondingly, its low bioavailability. Nanoparticle-stabilised emulsions of celecoxib were produced to assess the stability of the celecoxib in the formulation and, additionally, to determine whether the celecoxib could be satisfactorily released from the capsules. The capsule formulations, produced by spray-drying, were particularly evaluated for their physicochemical properties, in vitro dissolution profiles and in vivo pharmacokinetic parameters in a rat model.

Materials and Methods
Materials

Celecoxib (99.0%) was purchased from ChemPacific (Canada). Caprylic/capric triglyceride (Miglyol® 812) and soybean lecithin (containing >94% phosphatidylcholine and <2% triglycerides) were obtained from Hamilton Laboratories (Australia) and BDH Merck (Australia), respectively. Fumed hydrophilic silica nanoparticles (average primary particle diameter 7 nm) (Aerosil® 380) were supplied by Degussa (Germany). All other chemicals were of analytical grade and used as received. High purity (Milli-Q) water was used throughout the study.

Preparation of Capsules

A two-step process was used to prepare the capsules containing celecoxib (ie homogenisation followed by spray-drying of the silica-stabilised emulsions). The initial o/w emulsions were prepared as follows: 0.6% (w/w) lecithin was dissolved in 10% (w/w) oil (Miglyol® 812), followed by the addition of celecoxib (1% w/w); after dissolving the drug, Milli-Q water was added as the continuous phase. Two different capsules were produced. The first capsule (designated as CapA) was produced from emulsion A, which contained 50% (wt relative to the oil content) silica nanoparticles in the aqueous phase. The second capsule (designated as CapB) was produced from emulsion B, which contained 50% and 6% (wt relative to the oil content) of silica nanoparticles in the aqueous and oil phases, respectively. The coarse o/w emulsions were homogenised (Avestin® EmulsiFlex-C5 Homogeniser) under a pressure of 1000 bar for 5 cycles. The homogenised emulsions were tumbled for 12 h after addition of the silica nanoparticle dispersion. The silica-stabilised emulsions were then spray-dried (Mini Spray-dryer B-290, BÜCHI Labortechnik AG) to form capsules under the following conditions: emulsion flow rate 5 ml/min, aspirator setting 10, air flow rate 0.6 $m^3$/min, inlet and outlet temperature 160° C. and 85° C. As a control, a dry emulsion system stabilised by maltodextrin (300% wt relative to the oil content), loaded with equivalent amount of celecoxib, oil and lecithin contents, was produced in the same way as described above to serve as a positive control.

Physicochemical Characterisation of Capsules
Oil Content

The oil content of the capsules was determined using thermogravimetric analysis (TA Instruments). The capsules were heated at a scanning rate of 10° C./min from 20-600° C. under nitrogen purging. The oil was completely evaporated at 346° C. and the silica remained thermally stable. After correction for the water content of silica and spray-dried silica, the subtracted weight loss corresponded to the oil content of the capsules.

Solid State Characterisation

The degree of crystallinity of encapsulated celecoxib was monitored by differential scanning calorimetry (DSC) and X-ray powder diffraction (XRD). DSC analysis was performed using the TA Instruments Q100 differential scanning calorimeter. A 15 mg sample was heated in an aluminium pan at a rate of 5° C./min over a temperature range of 25-200° C., under a flow of dry nitrogen gas (80 ml/min). Instrument calibration was undertaken using an indium standard. Powder XRD patterns were obtained using Philips (PW 1050/25) X-ray diffractometer with CuKα radiation (45 kV, 35 mA). The samples were scanned between 10-50° (2θ) at a rate of 1.0°/min. The surface structure of the capsules was examined by scanning electron microscopy (JMS-5310LV, JEOL) at an accelerating voltage of 15 kV. The samples were mounted on double-faced adhesive tape, and sputtered with gold before imaging.

Re-Dispersibility

The reconstitution properties of the capsules and the maltodextrin-stabilised dry emulsion (MDE) were assessed based on changes in droplet size and zeta potential over a period of time as characterised by dynamic light scattering (DLS) and phase analysis light scattering (PALS), respectively, using a Malvern Zetasizer Nano instrument. Each formulation (5 mg/ml powder) was re-dispersed in phosphate buffer (0.05 M, pH 7.2) following the method of Jang et al. [20], and diluted 100-fold with Milli-Q water prior to measurement at 25° C. Size distributions are expressed as the z-average diameter together with the polydispersity index (PI). Zeta potentials are presented as mean±S.D. of three replicate measurements. Additional studies by laser diffraction was undertaken to confirm the presence of negligible particles of >10 μm.

Drug Loading Capacity

Drug loading capacity, expressed as the mass of encapsulated celecoxib divided by the mass of lipid load in percentage, was determined by a solvent extraction method (nb. the drug content was also used as a measure of chemical stability). The encapsulated celecoxib was extracted by dissolving 10 mg of the formulation powder in 2 ml of methanol (which has been tested to give 100±1% extraction efficiency). The supernatant (0.5 ml) was taken and the solvent was evaporated under a dry nitrogen stream at 30° C. (Pierce Reacti-Therm™ Heating Module). The resulting residue was redissolved in 10 ml of an acetonitrile:methanol:water mixture (50:10:40) (pH 3.5) by vortex-mixing for 1 min, and centrifuged at 9,400 g for 15 min prior to analysis for celecoxib content by using the HPLC method developed by Zarghi et al., 2006 (as described below).

HPLC Assays for Celecoxib

Celecoxib was assayed using a HPLC system (Hewlett Packard 1100) consisting of a series of G1310A isopump, G1313A auto sampler, G1314A variable UV detector (Shimadzu Corporation, Japan) set at 254 nm, and a LiChrospher $C_{18}$ analytical column (RP-18e, 100 mm×4.6 mm). The mobile phase was a mixture of acetonitrile, methanol, and water (50:10:40 v/v) containing 0.2% (v/v) glacial acetic acid (pH 3.5), eluted at a flow rate of 1.0 ml/min. The limit of detection (LOD) and the limit of quantification (LOQ) of this analytical method were 0.01 µg/ml and 0.05 µg/ml, respectively. The intra- and inter-day assay precision was assessed by coefficient of variance (<3% and <7%, respectively) and the accuracy was assessed as percentage bias (<5%). Linear calibration curves ($r^2$>0.99) were plotted for chromatographic peak areas against celecoxib concentrations (in mobile phase solution and phosphate buffers) over the range of 0.05-10 µg/ml, without the addition of an internal standard due to high specificity and reproducibility of the assay. All analytes were diluted suitably to establish a final concentration in the range for HPLC quantification.

Solubility and Dissolution Study

Solubility

The equilibrium solubility of celecoxib in phosphate buffer (0.05 M, pH 7.2) containing 0, 0.05, and 0.5% (w/v) sodium lauryl sulphate (SLS) was determined by adding an excess amount of celecoxib to 10 ml of each medium. The mixture was shaken in a thermostated mixer chamber (37° C.) for 48 h. Equilibrated samples were centrifuged at 9,400 g for 15 min to remove undissolved materials. The amount of celecoxib dissolved was assayed using the HPLC method outlined above.

Dissolution Study

The in vitro dissolution study was performed in 900 ml of phosphate buffer (0.05 M, pH 7.2) containing 0, 0.05, and 0.5% (w/v) SLS, using USP 23 type II apparatus (paddle method) operating at 75±0.02 rpm. Each sample, containing ~2 mg of celecoxib (equivalent to the amount used in the in vivo studies), was added into the dissolution medium maintained at 37±0.5° C. Aliquots of 3 ml were drawn at fixed time points and replaced with an equal volume of fresh dissolution medium. The drawn samples were centrifuged at 9,400 g for 15 min to remove undissolved materials. The supernatant was subjected to another cycle of centrifugation under the same conditions. An aliquot of 100 µl was taken from the middle portion of each centrifuged samples before diluted 2-fold with acetonitrile. Centrifugation was selected for phase separation of the samples because preliminary experiments showed that most (Millipore) filters absorb celecoxib, therefore separation by filtration was not employed. The amount of celecoxib dissolved in the dissolution media was analysed by HPLC as described previously.

In Vivo Absorption Study

Animal Experiments

Groups of 5 male Sprague-Dawley rats weighing 330±30 g were used for each absorption study. One group was dosed intravenously with 5 mg/kg celecoxib in PEG 400/saline (2:1 v/v) solution, while the other groups were administered orally with one of the six formulations at the same dose by oral gavage under light inhaled anaesthesia: celecoxib aqueous suspension, celecoxib-lipid solution, Celebrex®, MDE, Cap-A and Cap-B. Pure celecoxib and Celebrex® powder were suspended in 0.25% (w/v) sodium carboxymethylcellulose, while MDE (0.6-0.7 g powder) and capsules (0.15-0.2 g powder) were re-dispersed in Milli-Q water. The rats were cannulated in the right jugular vein under inhaled anaesthesia, allowed to recover, and fasted overnight (14±1 h) prior to each oral dosing and were given access to food 4 h post-dose, but water was accessible at all time. Blood samples (0.2 ml) were collected from the jugular vein at designated time intervals and the cannula was flushed with an equal volume of heparinised normal saline (50 units/5 ml) to prevent blood clotting. The collected blood samples were centrifuged at 9,400 g for 5 min. An aliquot of 100 µl plasma was vortex-mixed with 100 µl acetonitrile and centrifuged at 3,500 g for 10 min to remove proteins, prior to HPLC analysis as described before. Celecoxib content in the plasma samples was computed from the same calibration curve (celecoxib in mobile phase) without the use of plasma due to high extraction recovery of celecoxib. This was validated from an extraction recovery test in which blank plasma samples were spiked with three different concentrations of celecoxib working solutions and proteins were removed similarly. A blank plasma sample without the addition of celecoxib was treated in the same way. The recoveries of celecoxib in the plasma were determined to be 100±5%.

Pharmacokinetic Calculations

The pharmacokinetic parameters were determined using the PC software, WinNonlin® Standard Edition Version 4.1 (Pharsight Corp.), employing a non-compartmental model. The maximum plasma concentration ($C_{max}$) and the time at which $C_{max}$ is reached ($t_{max}$) were obtained from the individual plasma concentration-time curves. The area under the plasma concentration-time curve from time zero to infinity $AUC_{0-\infty}$ was calculated using the linear trapezoidal rule. The values of $AUC_{0-\infty}$ obtained were used to estimate the absolute bioavailability (F) according to Eq. (I):

$$F = \frac{AUC_{oral}(h \times mg/ml)}{AUC_{IV}(h \times mg/ml)} \times \frac{Dose_{IV}\ (mg)}{Dose_{oral}\ (mg)} \tag{1}$$

Statistical Analysis

The experimental data from different formulations were analysed statistically by one-way analysis of variance (ANOVA) with a Least Significant Difference (LSD) post-hoc test using the statistical package for social sciences (SPSS version 15.0) software, with the level of significance set at p<0.05.

Results and Discussion

Capsule Formation and Solid State Properties

The two-step formation process for capsules is schematically depicted in FIG. 1. Previously, the concerted stabilising effect of silica nanoparticles and lecithin for equivalent liquid emulsions has been reported when silica nanoparticles were initially added to the oil phase (emulsion B)(Eskander et al., 2007). This effect was not observed for emulsion A due to unfavourable adsorption of silica nanoparticles to the negatively-charged droplet interfaces. Therefore, the drying step is warranted to confer storage stability to the emulsions. As shown by the SEM image, both spray-dried Cap-A and Cap-B capsules consist of well-separated spherical structures with diameters of 1-5 μm, and these were not significantly different in their surface morphology. Examination of the cross-sectional morphology of both capsules demonstrated porous matrix structures with pore sizes ranging from 100-500 nm. This may be attributed to re-distribution and self-assembly of the silica nanoparticles from the continuous phase to the droplet surface and inner oil core during the water removal process. Therefore, the capsules formed appear not to be merely nanoparticle-coated core and shell structures as would be the case for existing dry emulsions which were described to be "spherical hollow particles" (Pedersen et al., 1998). The capsules formed are considered to provide a lipid vehicle for poorly soluble drugs due to the formation of the internal silica/lipid matrix. The oil loading levels for Cap-A and Cap-B, as determined by thermogravimetric analysis, were 51% (w/w) and 42% (w/w), respectively; with corresponding oil entrapment efficiencies of 100% and 92%.

hand-shaking and gentle vortex-mixing for ~30 seconds. Table 1 summarises the physicochemical properties of capsules and MDE re-dispersed in phosphate buffer (0.05 M, pH 7.2). Initially, after high pressure homogenisation and mixing with silica or maltodextrin dispersion, the emulsion droplets were in the size range of 0.2-0.5 μm (data not shown). The formation of larger capsules after spray-drying was attributed to particle/droplet agglomeration and re-distribution of the silica nanoparticles into the oil droplets. The mean droplet size of all re-dispersed formulations was <3 μm, with the observation that MDE re-dispersed to form relatively smaller droplets than the capsules. This was attributed to deposition of silica nanoparticles in the oil core of the capsules, in addition to the formation of a surface coating as in the case of MDE. The influence of the initial location of solid particles on the droplet sizes was negligible for capsules; that is, Cap-A and Cap-B were not significantly different in their droplet sizes after spray-drying and reconstitution. Despite of the high polydispersity (>0.4) observed upon reconstitution, the absence of larger droplet size fractions was further confirmed by laser diffraction.

TABLE 1

Physical and chemical stability of re-dispersed Celecoxib formulations stored at room temperature (mean ± S.D., n = 3)

| Celecoxib formulations | Storage (weeks) | Droplet size z-average (d · nm) | PDI | Zeta potential (mV) | Drug loading capacity in lipid (% w/w) |
|---|---|---|---|---|---|
| MDE | 0 | 448.7 ± 180 | 0.408 ± 0.12 | −66.3 ± 7.2 | NA |
|  | 3 | 593.9 ± 245 | 0.745 ± 0.22 | −53.5 ± 2.6 | 1.03 ± 0.02 |
|  | 8 | 877.7 ± 347 | 0.707 ± 0.19 | −49.7 ± 14.7 | 1.03 ± 0.02 |
| Cap-A | 0 | 2977.0 ± 800 | 0.883 ± 0.12 | −73.6 ± 14.7 | NA |
|  | 3 | 2444.3 ± 188 | 0.436 ± 0.05 | −46.2 ± 12.9 | 1.42 ± 0.03* |
|  | 8 | 2384.0 ± 222 | 0.660 ± 0.32 | −45.4 ± 8.1 | 1.42 ± 0.05* |
| Cap-B | 0 | 2241.0 ± 695 | 0.881 ± 0.03 | −41.9 ± 8.4 | NA |
|  | 3 | 1652.9 ± 673 | 0.696 ± 0.31 | −50.8 ± 1.4 | 1.63 ± 0.15* |
|  | 8 | 1954.8 ± 422 | 0.746 ± 0.05 | −62.3 ± 5.3 | 1.58 ± 0.05* |

*statistically higher than MDE ($p < 0.05$)

Figure 2:
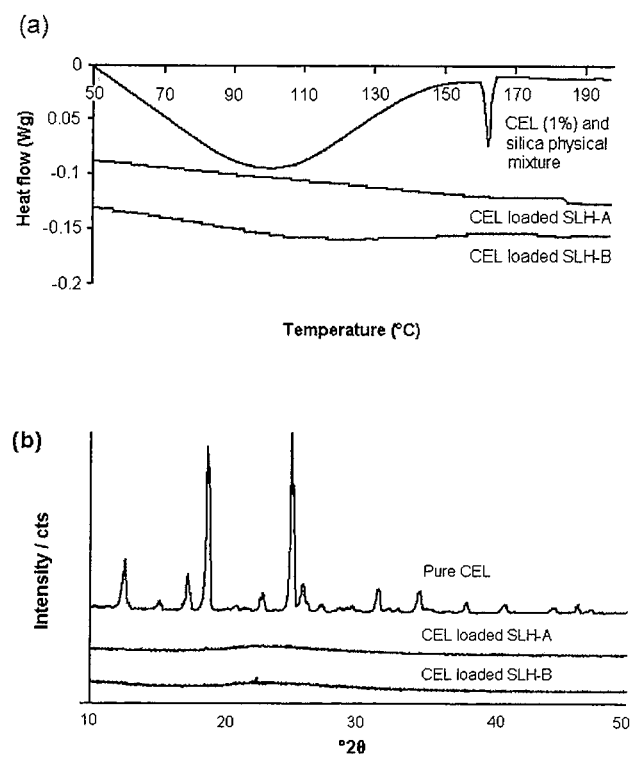
FIG. 2 provides graphical results showing the solid-state stability of celecoxib-loaded capsules described in Example 1: (a) DSC thermograms and (b) XRD profiles.

FIG. 2(a) shows the DSC thermograms of a physical mixture of celecoxib and silica nanoparticles, and celecoxib-encapsulated capsules. Celecoxib, when physically mixed with silica nanoparticles, exhibited a sharp melting endotherm at 161.7° C., indicating the presence of crystalline drug. The broad endotherm at ~100° C. resulted from evaporation of moisture from the mixture. The absence of an endothermic peak for the capsules suggested that the encapsulated drug was molecularly well-dispersed in the silica-lipid matrices, and complete drug amorphisation was attained. Presence of the amorphous, molecularly dispersed form of celecoxib in the capsules was further confirmed by XRD analysis. As depicted in FIG. 2(b), the sharp diffraction peaks of crystalline celecoxib (eg at 18.7° and 25.0° (2θ)), were not observed in the XRD patterns of celecoxib-encapsulated capsules. Extended analyses have shown non-crystalline celecoxib in these capsule formulations stored at room temperature for at least 6 months.

Re-Dispersibility and Colloidal Properties

The reconstitution properties of the capsules and MDE were evaluated after preparation and during storage at room temperature (for 3 and 8 weeks). Based on visual observation, both capsules and MDE were readily re-dispersed in aqueous solutions (ie Milli-Q water and phosphate buffer) by brief In addition to droplet sizes, the zeta potential and drug content of the capsules and MDE were well preserved over the study period (8 weeks), indicating considerable re-dispersibility and stability of the dry lipidic formulations stored at room temperature. The drug loading capacity (<2%) was limited by the solubility of celecoxib in Miglyol oil (~10 mg/ml), which is a common feature for lipid-based formulations. However, it was noted that both capsule samples exhibited a statistically higher drug loading level in comparison to MDE ($p<0.05$), possibly attributed to increased storage capacity through the inner porous matrix of the capsules. Further, celecoxib adsorption onto the silica nanoparticles may also occur during the homogenisation and spray-drying processes.

Solubility and Dissolution Study

Solubility

The solubility of celecoxib in a series of dissolution media containing different amount of sodium lauryl sulphate (SLS) was determined. The number of folds of saturation volume (FSV) provided by 900 ml of media for 2 mg celecoxib was estimated to assess the solubilising capacity of each media. The equilibrium solubility ($C_n$) of celecoxib in phosphate buffer containing 0, 0.05, 0.25, 0.5, and 1.0% of SLS was found to be 2.11±0.01 μg/ml (FSV 0.9), 2.33±0.15 μg/ml (FSV 1.0), 3.20±0.16 µg/ml (FSV 1.4), 8.00±0.39 µg/ml (FSV 3.6), and 119±29 µg/ml (FSV 53.6), respectively. According to the USP guideline, sink conditions are achieved if drug concentrations are maintained at or below one-third of the saturation solubility. It was observed that the solubility of celecoxib increased in a non-proportional fashion with the addition of SLS. A minimum level of 0.5% SLS was sufficient to provide sink conditions for celecoxib dissolution (FSV>3). In the following study, the dissolution pattern of pure celecoxib and the various celecoxib formulations was studied using both sink (0.5% SLS) and non-sink (0% and 0.05% SLS) conditions.

Dissolution Study

Figure 3:
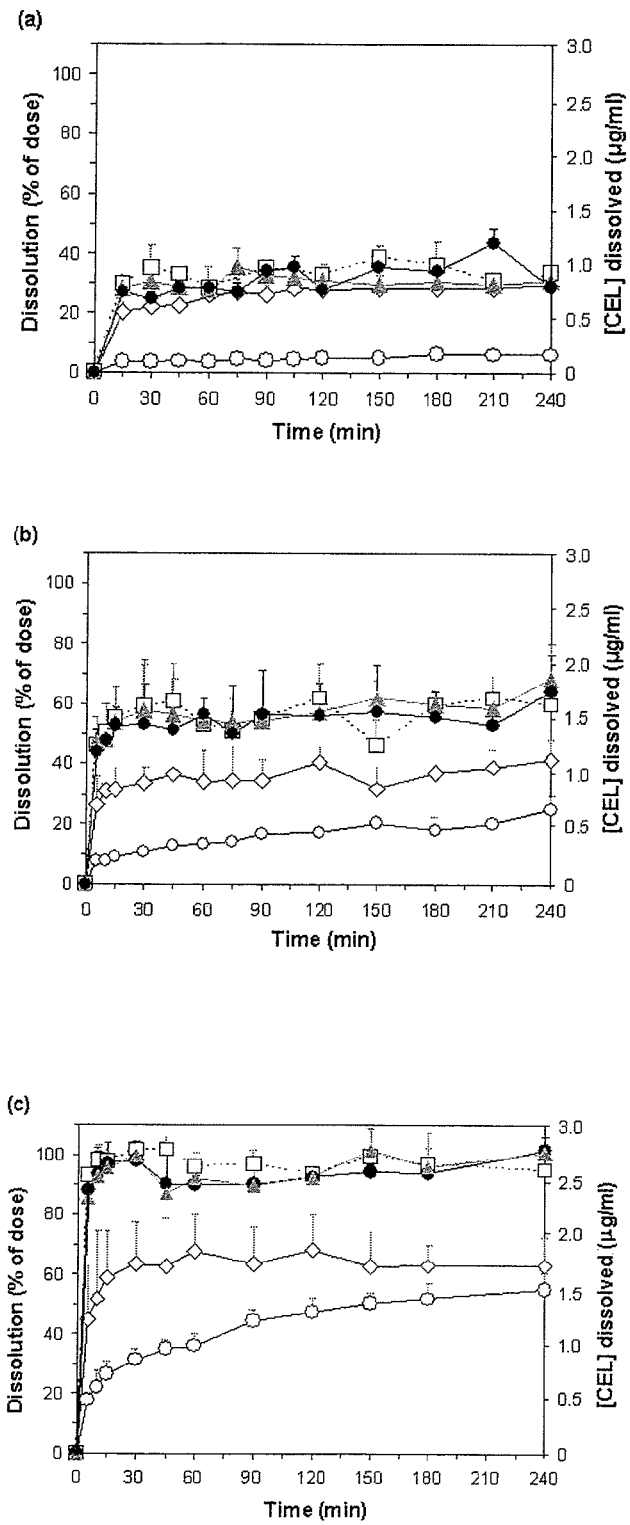
FIG. 3 shows the mean dissolution profiles of celecoxib (2 mg) in phosphate buffer (0.05 M, pH 7.2) containing (a) 0% SLS and (b) 0.05% SLS and (c) 0.5% SLS: Pure celecoxib (□), Celebrex® (◇), MDE (□), CAP-A (▨) and CAP-B (●) (mean±S.D., n=3)

SLS was employed as a wetting and solubilising agent in the dissolution medium for simulating the sink effect in the gastrointestinal tract. The dissolution profiles of celecoxib from various formulations are illustrated in FIG. 3. Pure celecoxib demonstrated the lowest rate and extent of dissolution at all times under both sink and non-sink conditions, due to its poor wettability and aqueous solubility. Celebrex®, MDE and capsules showed an initial fast release in the first 15-30 min followed by a slow release phase propagating to a plateau stage. The influence of silica nanoparticle layers of different hydrophobicity in controlling drug release from homogenised liquid emulsions has been previously investigated (Simovic et al., 2007). Here, the dissolution profiles of celecoxib from spray-dried capsules formulated with hydrophilic silica were obtained. Two dissolution parameters were evaluated from the study employing sink conditions: the dissolution efficiency (% DE), and the time to achieve 50% of drug dissolution ($t_{50\%}$) (Table 2). % DE is the area under the dissolution curve between two specified time points expressed as a percentage of the area of the rectangle described by 100% dissolution in the same time intervals, which can be calculated using Eq. (II):

$$\% \, DE = \frac{\int_{t_1}^{t_2} y \, dt}{y_{100}(t_2 - t_1)} \times 100 \quad (II)$$

where γ is the percentage of drug dissolved at time t. Taking pure celecoxib as the reference, capsules and MDE produced a 4- to 5-fold improvement in % DE at the initial stage (ie the first 5-15 min), and a 2-fold increment at the plateau phase of the dissolution process, double that observed for Celebrex®.

TABLE 2

Dissolution characteristics (with the number of fold of improvement compared to pure celecoxib) of various celecoxib formulations in phosphate buffer containing 0.5% SLS at 37° C. (mean ± S.D., n = 3)

| Celecoxib formulations | Dissolution efficiency (% DE)* | | | $t_{50\%}$ (min) |
|---|---|---|---|---|
| | t = 5 min | t = 15 min | t = 180 min | |
| Pure celecoxib | 8.9 ± 1 | 24.3 ± 5 | 48.9 ± 3 | 144.8 |
| Celebrex ® | 22.4 ± 9 (2.5) | 55.3 ± 19 (2) | 65.3 ± 12 (1) | 8.8 (16) |
| MDE | 46.6 ± 1 (5) | 98.0 ± 2 (4) | 96.6 ± 1 (2) | 2.7 (54) |
| CAP-A | 42.8 ± 3 (5) | 94.4 ± 7 (4) | 97.0 ± 5 (2) | 2.9 (50) |
| CAP-B | 44.2 ± 1 (5) | 95.3 ± 7 (4) | 93.3 ± 2 (2) | 2.8 (52) |

*p < 0.05

One mechanism for improved celecoxib dissolution from capsules and MDE is via enhanced dispersion of the lipid droplets in the aqueous medium attributable to the hydrophilic carriers (ie silica and maltodextrin). Secondly, the molecular state of the encapsulated drug also resulted in enhanced release kinetics. Since celecoxib is in a molecularly dissolved state (ie amorphous) in the lipid phase, the initial dissolution step, which was required in the case of pure drug and Celebrex®, does not need to take place from the lipid formulations. The initial burst drug release from the lipid formulations was mostly a result of the fast diffusion of the encapsulated drug to the droplet surface and into the medium. SLS, which aggregates to form micelles in aqueous solutions, plays an important role in driving the diffusion of amorphous celecoxib from the lipid phase into the surrounding aqueous medium. Under non-sink conditions, celecoxib could not fully release from the lipid-based formulations due to preferred distribution (partitioning) of the drug in the lipid phase. It was experimentally determined that the distribution ratio (log D) of celecoxib in Miglyol® oil and blank phosphate buffer was 3.7 (data not shown). The value of $t_{50\%}$ was substantially reduced by the lipid-based formulations, compared to pure celecoxib and Celebrex®. With the conventional assumption that the rate and extent of drug dissolution directly reflect the concentration of readily absorbable drug in the intestinal lumen, it was proposed that both capsules and MDE have the potential to enhance the oral absorption process. Interestingly, all three lipid-based systems successfully attained more than 85% of drug dissolution within 30 min under appropriate sink conditions, hence meeting the FDA criteria for classification as immediate-release dosage forms.

In Vivo Absorption Study

Figure 4:
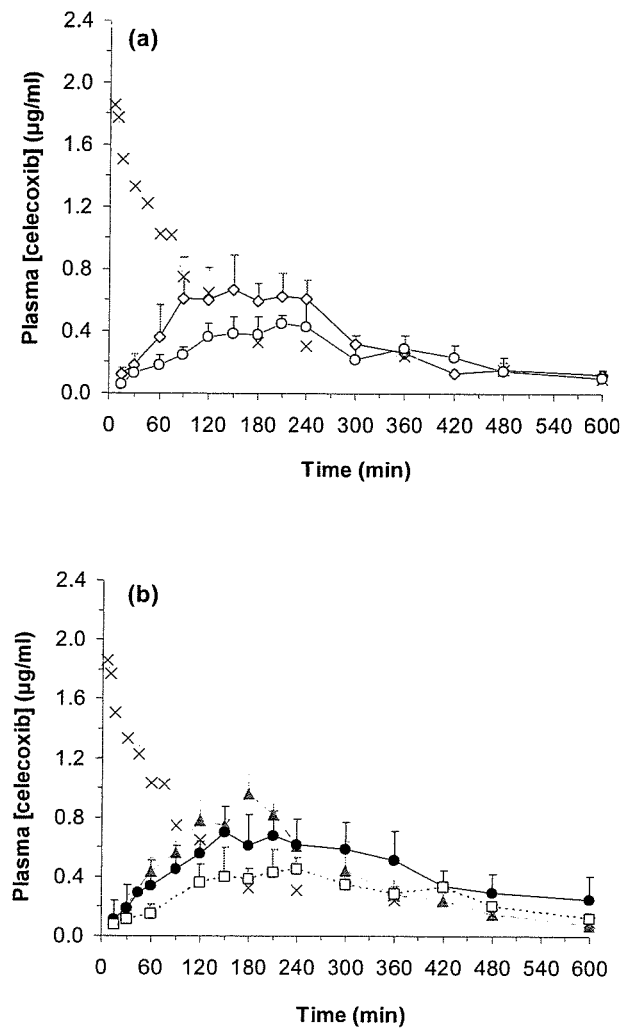
FIG. 4 shows the plasma concentration-time profiles of celecoxib in male Sprague-Dawley rats following an intravenous dose (X) and a single oral administration of various formulations equivalent to 5 mg/kg celecoxib: (a) celecoxib aqueous suspension (□) and Celebrex® (◇); (b) MDE (□), CAP-A (▨) and CAP-B (●) (mean±S.D., n=5)

The oral absorption of celecoxib from the various formulations (ie aqueous suspension, lipid solution, Celebrex®, MDE and capsules) was studied in a fasted rat model. The mean plasma concentration-time curves of celecoxib following a single dose of each formulation are presented in FIG. 4. The corresponding pharmacokinetic data is summarised in Table 3.

TABLE 3

Pharmacokinetic parameters of celecoxib following a single dose of various celecoxib formulations based on non-compartmental calculation (mean ± S.D., n = 5)

| Celecoxib Formulations | $t_{max}$ (min) | $C_0$ (μg/ml) | $AUC_{0 \to \infty}$ (min · μg/ml) | F (%) |
|---|---|---|---|---|
| I.V. injection | — | 1.86 ± 0.44 | 268 ± 67 | — |

| | $t_{max}$ (min) | $C_{max}$ (μg/ml) | $AUC_{0 \to \infty}$ (min · μg/ml) | F (%) |
|---|---|---|---|---|
| Oral control systems | | | | |
| Aqueous suspension | 202 ± 57 | 0.50 ± 0.16 | 167 ± 22 | 62 ± 8 |
| Lipid solution | 158 ± 29 | 0.44 ± 0.12 | 170 ± 35 | 63 ± 13 |
| o/w emulsion | 240 ± 112 | 0.49 ± 0.23 | 197 ± 78 | 73 ± 29 |
| MDE | 233 ± 62 | 0.51 ± 0.12 | 194 ± 13 | 72 ± 5 |
| Celebrex ® | 162 ± 45 | 0.63 ± 0.18 | 223 ± 35 | 83 ± 13 |
| Oral novel systems | | | | |
| Cap-A | 174 ± 33 | 1.00 ± 0.16[a,b,c] | 250 ± 35[a] | 93 ± 13[a] |
| Cap-B | 144 ± 54[b] | 0.74 ± 0.15[a] | 270 ± 60[a,b] | 100 ± 22[a,b] |

[a]statistically higher than aqueous suspension (p < 0.05)
[b]statistically higher than MDE (p < 0.05)
[c]statistically higher than Celebrex ® (p < 0.05)

Celecoxib aqueous suspension gave the lowest bioavailability in fasted rats (62%). Statistical analysis showed that the pharmacokinetic data obtained for celecoxib-lipid solution, o/w emulsion, MDE and Celebrex® were not significantly different from that of the aqueous suspension. Interestingly, the capsule formulations (particularly Cap-B) dramatically increased the fasted-state absorption, giving a superior bioavailability (93-100%) in comparison to o/w emulsion and MDE (p<0.05), although the latter two formulations have relatively smaller droplet sizes. It is apparent that differences in the initial droplet size did not have a pronounced effect on the extent of celecoxib absorption. In vivo performance of lipid-based systems is believed to be mostly governed by the interaction between formulation lipids and the secreted bile contents in the intestinal lumen. Three major mechanisms have been described to rationalise how lipid-bile interaction can facilitate drug absorption (Boyd et al., 2007; Humberstone et al., 1997). First, the formation of colloidal and liquid crystalline structures resulting from bile, lipids and other endogenous secretions keeps the poorly soluble drug solubilised in the intestinal fluid with reduced precipitation. Drugs solubilised in the mixed micelecoxiblar phases can then diffuse easily through the pre-epithelial unstirred aqueous layer to the absorptive site. The third mechanism involves an alteration to the intestinal permeability induced by the lipid-bile interaction in which the solubilised drug molecules can be absorbed via the paracelecoxiblular or the transcelecoxiblular routes. It should be noted that rats do not possess a gallbladder as do humans, therefore there is always a continuous secretion of bile salts into the gastrointestinal tract even without stimulation by lipids or food. This may explain the negligible improvement of celecoxib absorption by the lipid solution and o/w emulsion in fasted rats.

The capsules were also shown to exhibit a statistically higher $C_{max}$ in comparison to other tested formulations (p<0.05). Although the differences in the overall bioavailability of capsule formulations and Celebrex® are less obvious from the current study employing a relatively low dose of celecoxib (5 mg/kg), the noticeable increment in $C_{max}$ observed particularly for Cap-A (approximately 1.5-fold improvement) suggests that it would be possible to reduce the required dose with this formulation. Assuming that the minimum effective pain-relieving plasma concentration is ~155 ng/ml celecoxib as reported for humans based on the inhibitory effect on prostaglandin E2, it can be expected that Cap-B has potential to provide a prolonged therapeutic effect as compared to other formulations (ie mean plasma concentration equals to 0.25 μg/ml at 10 h). Further, considering that the usual prescription dose for celecoxib is 100-400 mg per day, the applicability of capsule formulations to this drug is to some degree limited by the current drug loading level (ie a large dosage of carrier would be required). Nevertheless, capsules offer potential therapeutic value to other poorly soluble drugs with lower required dosage by modifying their pharmacokinetic properties (e.g. AUC, $C_{max}$), and hence allowing lower effective doses to be prescribed for better or at least equivalent therapeutic efficacy, as well as improved therapeutic cost-effectiveness and safety, namely by minimising inter-subject variations caused by food intake. The present study will provide the impetus for studies on a range of other poorly soluble drugs.

In Vitro-In Vivo Correlation (IVIVC)

Figure 5:
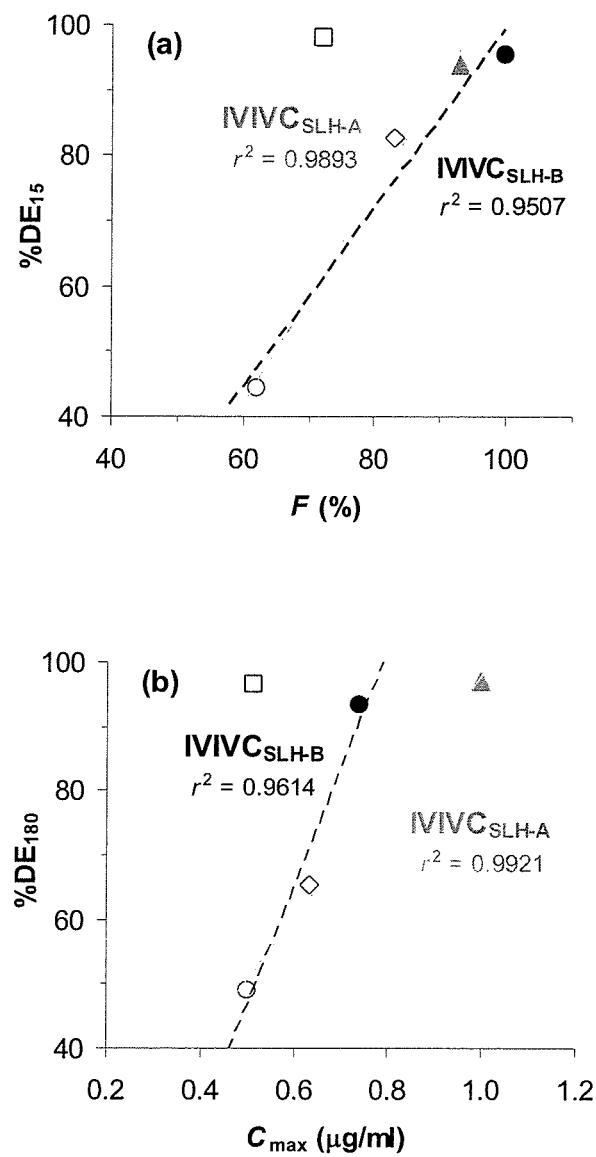
FIG. 5 provides single-point correlations of pure celecoxib (□), Celebrex® (◇), MDE (□), and capsule formulations Cap-A (▨) and Cap-B (●): (a) % $DE_{15}$ correlated to absolute bioavailability; (b) % $DE_{180}$ correlated to maximum plasma concentration.

Conventionally, correlation between the drug dissolution or release profiles and the absorption data has been regarded as the most suitable IVIVC model for BCS Class II compounds, since their oral absorption is mainly rate-limited by the dissolution process in the gastrointestinal medium. The concept of dissolution efficiency (% DE) is a useful parameter to be correlated with the corresponding in vivo bioavailability ($AUC_{0 \to \infty}$ or F), because both variables are estimated by the integration of the area under the curves. In this example, single-point correlations were observed for pure celecoxib, Celebrex®, Cap-A and Cap-B by using the mean data values obtained. As shown in FIG. 5, the dissolution efficiency at the initial dissolution stage (ie % $DE_{15}$) was found to be linearly correlated with F, whereas % $DE_{180}$ was well-correlated with the values of $C_{max}$, which was estimated to be reached at the same time point ($r^2 > 0.9$).

Bearing in mind that the capsule and MDE formulations are composed of similar lipid and emulsifier contents, the variation in the absorption results is expected to lie in the types of the stabilisers used. Since silica nanoparticles and maltodextrin did not produce a significant difference in drug dissolution, it is hypothesised that the specific capsules structure and the presence of silica nanoparticles enhanced drug absorption from the capsule formulations via a different mechanism other than improved dissolution.

Conclusions

A silica-lipid hybrid capsule formulation system was successfully developed to enhance the in vitro dissolution and in vivo absorption of the poorly soluble drug, celecoxib. The readily re-dispersible capsule formulations have excellent physicochemical stability at room temperature for at least 6 months. In conjunction with the increased rate and extent of in vitro dissolution, the capsule formulations exhibited improved fasted-state bioavailability and a statistically higher $C_{max}$ in comparison to aqueous suspension, lipid solution, o/w emulsion, maltodextrin-stabilised dry emulsion and Celebrex®. Linear correlations were established based on % DE with F and $C_{max}$. Thus, capsules have emerged as a novel approach to enhance the oral absorption of poorly soluble anti-inflammatory drugs, with the potential to improve their therapeutic efficacy and cost-effectiveness.

Example 2

Nanoparticle-Stabilised Indomethacin Capsule Formulation

Materials and Methods

Materials

High-purity water (Milli-Q) was used throughout. Lecithin and oleylamine were supplied by Aldrich (USA). The oil phase used was fractionated triglyceride coconut oil (Miglyol812N) supplied by Hamilton Laboratory (Australia). Pancreatin (porcine) and bile extract (porcine) were purchased from Sigma-Aldrich (USA). 4-bromobenzeneboronic acid (BBBA) was purchased from Lancaster, Germany. Phosphatidylcholine Epikuron 200 (purity, minimum 92%) was purchased from Degussa, Germany. Fumed silica nanoparticles Aerosil® 380 (Degussa) have a BET surface area of $380\pm30$ $m^2g^{-1}$ and 2.5 Si—OH groups $nm^{-2}$ (determined from Li—Al-hydride method). Contact angles estimated from enthalpy of immersion data are reported[21] to be 14° (water/air) and 0° (toluene/water). Indomethacin (Sigma Aldrich) has a water solubility (pH=7.2) of 0.768 mg/ml, pKa of 4.5 and logP of 3.6.

Preparation and Characterisation of Pickering Emulsions

Lecithin or oleylamine (0.6 or 1 wt %, respectively) was dissolved in the oil phase (with or without 10 wt % indomethacin), added into the silica nanoparticle aqueous dispersion prepared using an ultrasonic bath (Labec, model J-LTB3) (300 W for 2 hours) under hand mixing and passed through a high pressure homogeniser (Avestin EmulsiFlex—C50 High Pressure Homogenizer) for 5 cycles under pressure 5 mbar. Diluted Pickering emulsions were analysed for size and zeta potential using a Malvern Zetasizer Nano ZS. A freeze-fracture SEM technique (Philips XL 30 FEG scanning electron microscope with Oxford CT 1500 cryotransfer system) was used to image the nanoparticle coated emulsions prior to drying. The methodology consisted of emulsion cryofixation, fracturing, etching, platinum coating and imaging. Emulsion samples (50 μL) were deposited on a flat copper substrate holder and cryofixed by rapid cooling with liquid nitrogen (−196° C.) in order to reach the vitreous state. Frozen samples were then mounted on a cold table under liquid nitrogen and then inserted into the freeze-fracture equipment at −150° C. and $10^{-6}$ Torr. A single-edge scalpel blade pre-cooled to −150° C. was then used to induce the fracture. Surface ice was removed during a sublimation step (ie by increasing the sample temperature to either −92 or −100° C. for a period of 2-5 min). Care is necessary during this step in order to avoid droplet disintegration. The fractured and etched sample was then sputter-coated with platinum (~2 nm), prior to SEM imaging. Energy dispersive analysis of X-rays (EDAX) was used during imaging to elucidate the chemical nature of the observed features.

Preparation and Characterisation of Dry Capsules

Nanoparticle containing emulsions, in the absence and presence of encapsulated indomethacin (10 wt % in the oil phase), were spray-dried (Buchi 190 Mini Spray Dryer) at a flow rate of 5 ml/min., aspirator setting 10, air flow 0.6 $m^3$/min, inlet temperature 160° C. and outlet temperature 85° C. The XPS spectra of dry capsules were recorded using a Kratos AXIS Ultra DLD spectrometer with a monochromated A1Kα radiation source (hv=1486.7 eV) operating at 15 kV and 10 mA. The pressure in the vacuum chamber during the analysis was less than $10^{-10}$ bar, and the take-off angle of the photoelectrons was perpendicular to the sample. The areas under selected photoelectron peaks in the spectrum were used to calculate the atomic concentrations. High-resolution (0.1 eV) spectra were then recorded for pertinent photoelectron peaks at a pass energy of 20 eV to identify the chemical state of each element. All the binding energies (BEs) were referenced to the C1s neutral carbon peak at 285 eV, to compensate for the effect of surface charging. The processing and curve-fitting of the high resolution spectra was performed using CasaXPS™ software. The analysis area was 700×300 μm. The oil encapsulation (ie the oil level within the capsules was determined using thermogravimetric analysis (TA Instruments)). Dry capsules were heated from 20° C. to 600° C. at a scanning rate of 10° C. $min^{-1}$ in nitrogen. The oil evaporated at 346° C. and the silica remained thermally stable. After correction for the water content of silica and spray dried silica, the observed weight loss corresponded to the oil content of the dry capsules. Oil entrapment efficiency was calculated based on the initial oil:silica weight ratio. The surface structure of the capsules was examined by SEM (JMS-5310LV, JEOL) at an accelerating voltage of 15 kV. The samples were mounted on a double-faced adhesive tape, and sputtered with gold before imaging. An FEI FIB201 focused ion beam instrument was used for sectioning and high-resolution imaging. The instrument is capable of producing a gallium ion beam of between 7 nm (at 1 pA beam current) and 300 nm (at 12 nA) in diameter at 30 keV energy. A platinum organometallic gas injector allows ion beam assisted deposition of platinum over selected areas of the sample, and this facility was used prior to the sectioning in order to alleviate sample charging from the insulating specimens. For sample sectioning, a large ion current (12 nA) was used initially to remove material by sputtering. A finer beam of lower current was then used to "polish" the vertical face of the sample by scanning the beam in a line and moving it progressively up to remove further material. The sample was then tilted to 45° and the polished face imaged using the same ion beam, at a much lower beam current to achieve the high-resolution ion beam induced secondary electron images shown here. BET surface area and pore volume of spray-dried capsules after oil removal by hexane extraction were determined by $N_2$ adsorption using a Micrometrics ASAP 2010 porosimeter.

Drug Encapsulation In Vitro Dissolution Tests and Digestion Experiments

The degree of crystallinity of indomethacin after preparation and 6 months storage under accelerated conditions (40° C. and 75% RH) was determined by differential scanning calorimetry (DSC) and X-ray powder diffraction (XRD).

DSC was performed using TA Instruments Q100 differential scanning calorimeter. A 15 mg sample was heated in an aluminium pan at a rate of 278.15 K/min over a temperature range of 25-200° C., under a flow of dry nitrogen gas (80 ml/min). Instrument calibration was undertaken using an indium standard. Powder XRD patterns were obtained using Philips (PW 1050/25) X-ray diffractometer with CoKα radiation (45 kV, 35 mA). The samples were scanned between 10-50° (2θ) at a rate of 1.0°/min. The amount of indomethacin in the capsules was determined using a HPLC method (based on a modified previous study[24]). The HPLC system (Hewlett Packard 1100) consisted of a series G1310A isopump, G1313A auto sampler and G1314A variable UV detector (Shimadzu Corporation). Separation was achieved using a LiChrospher 100 RP-18 analytical column (5 μm, 100 mm×4.6 mm i.d.). The isocratic mobile phase consisted of acetonitrile: water (65:35, v/v) containing 0.1% acetic acid. All chromatographic separations were performed at room temperature at a flow rate of 1 mL/min. The column eluent was monitored at a wavelength of 320 nm. The run time of each injection was set at 10 min and the injection volume was 50 μL. The dissolution tests under sink conditions were performed using a USP paddle system (Vankel) and kept at a controlled 37° C. Twenty five mg of pure indomethacin powder and dry capsules containing 25 mg of pure indomethacin were used for dissolution tests. The dissolution vessel contained 900 mL of phosphate buffer at pH 7.2 to simulate intestinal fluid. The paddle was rotated at 50 rpm. Samples (5 mL) were taken every 15 minutes for 3 h. The 5 mL removed was replaced using fresh phosphate buffer at 37° C. Five hundred μL of the sample was added to an Eppendorf tube and centrifuged (Sigma 1-15 centrifuge, Quantum Scientific) at 8000 rpm for two minutes. Supernatant (200 μL) was removed and placed in another tube. 200 μL of HPLC grade acetonitrile was added. The samples were measured using HPLC.

In vitro digestion experiments were performed according to standard methods. Briefly, 0.1 g of lipid (indomethacin solution in Miglyol containing 0.6% lecithin, equivalent submicron emulsion and capsule) was dispersed in 20 mL of digestion buffer (50 mM TRIS maleate, 150 mM NaCl, 5 mM $CaCl_2 \cdot 2H_2O$, pH 7.5) containing 5 mM NaTDC and 1.25 mM PC (conditions broadly representative of fasted state intestinal conditions). Experiments were performed at 37° C. in a stirred and thermostated glass vessel and were initiated by the addition of 3 mL of pancreatin extract containing 40000 tributyrin units (TBU) of pancreatic lipase (final lipase concentration of 1000 TBU per mL digest). Lipolysis was followed over 60 min using a pH-stat titration unit (Radiometer, Copenhagen, Denmark), which maintained the pH at 7.5. The fatty acids produced on lipolysis were titrated with 0.6 M NaOH. Aliquots (1.4 mL) were taken from the digestion medium at 5, 10, 15, 30, 45 and 60 min and a lipolysis inhibitor (0.5 M 4-BPB in methanol, 9 μL/mL digestion medium) immediately added to each sample to prevent further lipolysis. Samples were subsequently ultracentrifuged for 30 min at 37° C. and 334000 g (Optima XL-100K centrifuge, SW-60 rotor, Beckman, Palo Alto, Calif.) in order to separate the digests into an aqueous phase and a pellet phase. Samples obtained from each separated phase were assayed for indomethacin content by HPLC as described previously. Blank digestion experiments were also performed to account for the fatty acids produced on digestion of the lecithin present in the digestion media. Lecithin samples typically contained small quantities of glycerides (1% w/w triglyceride; 6% w/w diglyceride, <1% w/w fatty acids) and PC which is hydrolysed by phospholipase $A_2$ (present in pancreatin) to produce fatty acids and lyso-PC. Blank digestion experiments were therefore performed in the same manner as that described above, but in the absence of the added formulation. The digestion data obtained for the experimental formulations were subsequently corrected for background fatty acid production (ie fatty acids derived from the lecithin present in the digestion media) by substraction of the fatty acids produced during blank digestion experiments.

After dissolution tests for 4 hours and lipolysis for 1 hour, filtered and air dried capsules were imaged by SEM method described above. The oil content in dried and filtered capsules after 10 min. was determined by TGA.

In Vivo Bioavailability Studies

Groups of 5 male Sprague-Dawley rats weighing 320±20 g were used for the absorption study. One group was dosed intravenously with 1.78 mg/kg indomethacin in PEG 400/saline (2:1 v/v) solution, while the other groups were administered orally with one of the following formulations at the same dose by oral gavage:indomethacin aqueous suspension, indomethacin o/w liquid lecithin based submicron emulsion and indomethacin capsules according to the present invention. Pure indomethacin powder was suspended in 0.25% (w/v) sodium carboxymethylcellulose, while capsules were re-dispersed in Milli-Q water at a suitable concentration. The cannulated rats were fasted overnight (14±1 h) prior to each oral dosing and were given access to food 4 h post-dose, with water was accessible at all time. Blood samples (0.2 ml) were collected from the jugular vein at designated time intervals 0.083, 0.25, 0.5, 1, 1.5, 2, 2.5, 3, 4, 6, 8, 24 h post-dose, and the cannula was flushed with an equal volume of heparinised normal saline (50 units/5 ml) to prevent blood clotting. Blood samples (about 200 μL) were collected in heparinised 1.5 ml polythene tubes immediately at different times after dosing, and centrifuged at 800 rpm for 10 min at 4° C. Ten aliquot of 100 μL of plasma sample, 10 μL of acemetacin as an internal standard (IS, 20 μg/ml) was mixed for 30 s. After addition of 200 μL of acetonitrile with 0.1% acetic acid, the mixture was vortex-mixed for 1 min and centrifuged at 10000 g for 10 min to remove proteins. Indomethacin content in the supernatant was determined by HPLC. The chromatographic separation was performed using an Alltech Lichrospher 100 RP-18 (4.6 mm×250 mm, 5 μm) analytical column. The mobile phase consisted of a mixture of 0.1% (v/v) acetic acid in methanol: acetonitrile:distilled water (60:20:20 v/v), ultrasonically degassed prior to use. The mobile phase was delivered at a flow-rate of 1.0 ml/min, the detection wavelength was 320 nm, the attenuation was 0.001 and the injection volume was 20 μL. The pharmacokinetic parameters were determined using the PC software, WinNonlin® Standard Edition Version 4.1 (Pharsight Corp.), employing a non-compartmental model. The maximum plasma concentration ($C_{max}$) and the time at which $C_{max}$ is reached ($t_{max}$) were obtained from the individual plasma concentration-time curves. The area under the plasma concentration-time curve from time zero to infinity ($AUC_{0 \to \infty}$) was calculated using the linear trapezoidal rule. The values of $AUC_{0 \to \infty}$ obtained were used to estimate the absolute bioavailability (F) according to Eq. (1) above.

The experimental data from different formulations were analysed statistically by one-way analysis of variance (ANOVA) coupled with the Least Significant Difference (LSD) t-test using the statistical package for social sciences (SPSS version 15.0) software, with the level of significance set at $p<0.05$.

Results and Discussion

Formation of Capsules

Effective capsule formation was found to be dependent on the interfacial structure of the nanoparticle containing emulsions, which is in turn controlled by the surfactant charge and nanoparticle to lipid ratio. Lecithin confers negative charge to the emulsion droplets and the presence of silica nanoparticles (zeta potential, $\zeta=-27\pm2$ mV) has no significant effect on the droplet size and $\zeta$. Previous investigations by the present applicant on droplet-nanoparticle attachment has indicated the presence of bare and partially coated negative droplets even if the silica nanoparticles are present in amounts that are well above the level for monolayer formation. By contrast, positive droplets (oleylamine containing) are electrostatically coated by oppositely charged silica nanoparticles. The interaction is dependent on the nanoparticle-to-lipid ratio: (i) droplets are positively charged up to 5 wt % silica, (ii) droplets are neutralised and aggregated (to ~4.5 µm) at 6-10 wt % silica and (iii) droplets are charge reversed and slightly aggregated (to ~1.5 µm) at ≥10 wt % nanoparticles. Freeze fracture SEM images reveal partial, monolayer and multilayer coatings on the droplets at 5, 10 and 30 wt % silica, respectively. Theoretically, 40 wt % of silica nanoparticles (~50 nm) is required for a hexagonally close packed monolayer at the interface of ~0.5 µm droplets. Droplet flocculation occurs in the neutralised region due to the bridging between oppositely charged patches on partially coated droplets. Multilayer coatings in the charge reversed region reduce the level of size enlargement.

It is significant that free flowing dry capsules with good re-dispersability properties can be prepared from both negative and positive droplets. However, positive droplets form capsules at 10 times lower levels of silica (ie positive droplets require at least 5 wt % silica relative to droplets, whereas negative droplets require a minimum of 50 wt % silica). This difference in behaviour is a consequence of the different nanoparticle coating levels of negative and positive droplets. The exact boundary between barrier-controlled and barrier-less nanoparticle adsorption (and hence three phase wetting) depends not only on particle and droplet size, surface potentials, Hamaker constant, hydration forces, but also on the hydrodynamic force applied during mixing. For instance, the intensity of stirring has a significant impact on the concentration of particles required to obtain stable emulsions (ie higher particle concentrations are required to obtain stable emulsions by mild stirring in comparison with jet-homogenisation, where hydrodynamic forces are sufficient for particles to scale the energy barrier to adsorption). In this example, the hydrodynamic forces experienced by droplet-nanoparticle mixtures during high pressure homogenisation and spray drying are considered to promote adsorption and facilitate silica nanoparticle transport into the oil phase and hence the establishment of a three dimensional matrix structure.

Capsules from both negative and positive droplets have diameters in the range 1 to 5 µm. However, the external texture of the capsule is dependent on the droplet type and mirrors the emulsion's interfacial structure. That is, negative droplets form capsules with smooth surfaces and positive droplets and silica form capsules with rough surfaces (ie structured nanoparticle surface layers are visible); this is considered a consequence of the strong electrostatic attraction between the positive droplets and nanoparticles, hence greater stability of aggregate structures. Cross-sectional SEM imaging has confirmed the internal porous matrix structure for capsules prepared from both negative and positive droplets. In general, the pore size range for capsules from negative droplets is in the range from 100-500 nm, whereas capsules from positive droplets have a higher proportion of 25-100 nm pores. Average pore diameter determined by BET gas adsorption was 20 nm for both spray-dried silica nanoparticles and capsules after oil extraction. BET surface area for spray-dried silica nanoparticles without oil is 311 $m^2/g$ and for capsules after oil extraction with hexane 184 $m^2/g$; the difference in surface areas may be regarded as a consequence of oil entrapment.

Hydrophilic nanoparticles do not generally adsorb at the surface of emulsion droplets and consequently do not stabilise emulsions. Hydrophilic silica nanoparticles are an attractive encapsulating material especially for drug delivery purposes due to their high level of biocompatibility, however they cannot be used for encapsulation of emulsion droplets unless an additional driving force for attachment is provided.

The reduction of the electrostatic repulsion and hydration interactions between the particles and droplets represents one possible attachment strategy. Addition of oppositely charged hydrophilic surfactant may promote particle adsorption at the surface of the oil droplets, but only in the narrow region where droplets and particles are oppositely charged. A surplus of hydrophilic surfactant causes its adsorption at the surface of both droplets and particles and, consequently, diminishes electrostatic droplet-particle electrostatic attraction. The strategy employed here for nanoparticle coating of droplets based on electrostatics uses lipophilic molecules, initially added in the oil phase and located exclusively at the interface so that competitive adsorption at oil-water and nanoparticle-water interfaces is avoided.

X-ray photoelectron spectroscopy (Table 4) shows that the capsule surfaces are composed of both silica and carbon from the oil phase and emulsifiers. Thus, the capsule surface has a dual hydrophilic-lipophilic character. The carbon surface coverage is dependent on the oil:silica ratio for capsules based on positive droplets (Table 4). Further, the position of the Si 2p photoelectron peaks (Table 4) show chemical changes in the surface silica form (ie both $SiO_2$ and silicate are present for capsules composed of 5-10 wt % silica, whereas for >10 wt % silica only $SiO_2$ is observed); these differences are considered to be due to a greater proportion of charge neutralisation between silica and the amino groups from oleylamine at lower silica levels (small surface nitrogen XPS signal are also observed).

TABLE 4

Characteristics of dry capsules

| Sample [a] | Si2p (%) [b] | N1s (%) 398.59 eV | C1s (%) 283.39 eV | Oil loading [c] | Re-dispersability (pH = 2) | | Re-dispersability (pH = 7) | |
|---|---|---|---|---|---|---|---|---|
| | | | | | z-average size (µm) | zeta potential (mV) | z-average size (µm) | zeta potential (mV) |
| L50% | 11.35 100 0 | 0 | 53.45 | 50.67 | 1.6 | −18.3 ± 8.76 | 3.05 | −28.7 ± 10.7 |
| OA 5% | 5.19 91.9 | 0.16 | 72.69 | 80.44 | 1.74 | +72.5 ± 9.8 | 3.71 | +11.6 ± 14.1 |

TABLE 4-continued

Characteristics of dry capsules

| Sample [a] | Si2p (%) [b] | N1s (%) 398.59 eV | C1s (%) 283.39 eV | Oil loading [c] | Re-dispersability (pH = 2) | | Re-dispersability (pH = 7) | |
|---|---|---|---|---|---|---|---|---|
| | | | | | z-average size (μm) | zeta potential (mV) | z-average size (μm) | zeta potential (mV) |
| OA10% | 11.14 96.8 | 0.082 | 56.76 | 78 | 0.603 | +71.7 ± 15.4 | 2.15 | −8.11 ± 6.26 |
| OA15% | 11.53 100 | 0 | 52.49 | 74.5 | 1.2 | +68.8 ± 15 | 2.3 | 5 ± 6.2 |
| OA20% | 15.5 100 | 0 | 48.85 | 84.27 | 1.47 | +65.9 ± 27.4 | 3.14 | 6.02 ± 7.44 |
| SDS | 27 100 | 0 | 4.87 | | 1.5 | −5.42 ± 3.28 | 2.5 | −25 ± 8.6 |
| HS | 27.33 100 | 0 | 3.67 | | | | | |

[a] Sample labels: L—lecithin based; OA—oleylamine based; SDS—spray dried silica; HS—heated silica to 160° C. and cooled to room temperature; numbers on right-hand side- wt % silica relative to droplets in the aqueous phase
[b] Numbers on left-hand side- SiO$_2$ matrix at 102.92 eV, right hand side- silicates at 101.63 eV,
[c] determined by thermogravimetric analysis.

The oil content (from thermogravimetric analysis) is ~50 wt % for negative and significantly greater (75-85 wt %) for capsules prepared from positive droplets (in comparison the spray dried product from hydrophilic silica nanoparticles and oil without emulsifiers which contained ~5 wt % oil). The capsules show excellent re-dispersibility in acidic (pH=2) and neutral (pH=7) aqueous media (Table 4); this is equivalent to the re-dispersion behaviour of spray dried silica. In general, the capsules re-disperse to smaller sizes at pH 2 in comparison to pH 7. The re-dispersibility of dry capsules prepared from positive droplets mirrors their coating level in the initial Pickering emulsions (ie due to surface expression of amino groups). At pH 7, capsules prepared from partially neutralised emulsions remain positively charged, whereas those prepared from charge reversed Pickering emulsions are negatively charged when re-dispersed (Table 4). In acidic media, all oleylamine capsules are positively charged, with the highest positive value for capsules prepared from partially neutralised capsules.

Solid State Stability

Figure 6:
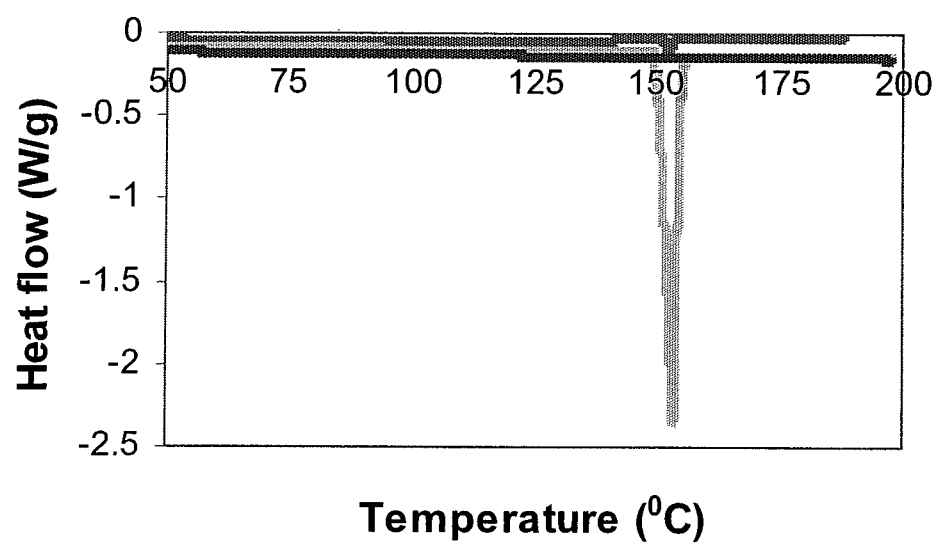
FIG. 6 provides DSC thermograms for pure and encapsulated drug (crystalline drug peak disappears in capsules and is absent during storage under accelerated conditions)
Figure 7:
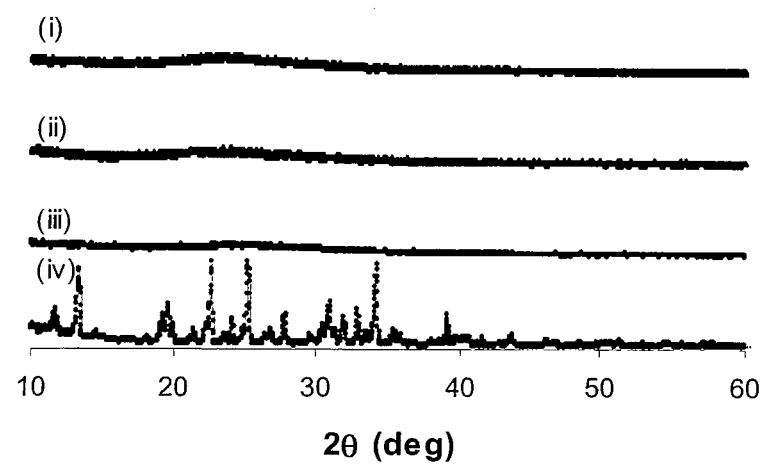
FIG. 7 provides XRD patterns of indomethacin in: (i) indomethacin containing capsules after 6 months storage; (ii) indomethacin capsules after preparation; (iii) drug free capsules; (iv) physical mixture indomethacin: microcapsules 0.01:1.

The capsules show many properties that are attractive for pharmaceutical application. First, they can encapsulate lipophilic compounds in amounts well above their solubility in the pure oil phase (eg indomethacin has been encapsulated into capsules at concentrations several times higher than its solubility in the oil phase). FIG. 6 shows the DSC thermograms of the pure drug and encapsulated indomethacin. Indomethacin exhibited a sharp endothermic peak at 159.4 C. for the melting of the stable γ-form. The absence of an endothermic peak for capsules suggested that the encapsulated drug was molecularly dispersed in the lipid matrices, and no crystalline drug was detected even after 6 months storage under accelerated conditions (75% RH and 40° C.). Considering the limitations of DSC to detect small crystals, XRD analysis was also conducted (FIG. 7), which is considered to be more sensitive to the presence of small crystals. XRD analysis clarified the presence of the stable γ-form in physical mixtures and no crystalline drug in the capsules after accelerated storage conditions (FIG. 7). It is well documented that indomethacin in stable γ-form is partially transformed into the meta-stable α-form upon spray drying and is then recrystalised back into the stable γ-form upon storage (Takeuchi et al., 2005).

Drug Dissolution In Vitro

Figure 8:
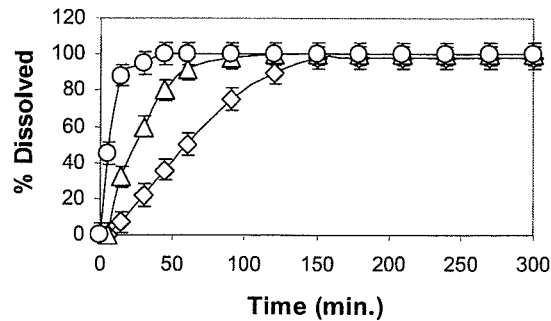
FIG. 8 provides the mean dissolution profiles of indomethacin (25 mg) in phosphate buffer (0.05 M, pH 7.2) under sink conditions: (◇) pure indomethacin; (Δ) o/w lecithin stabilised submicron emulsion; (□) capsules.

The dissolution profiles of indomethacin from o/w emulsions and capsules are shown in FIG. 8. The pattern of dissolution was found to be consistent for capsules with an initial fast release and complete dissolution after 15 min. Pure indomethacin demonstrated the lowest rate of dissolution at all times over a four-hour period. Two parameters were evaluated: the dissolution efficiency (% DE) and the time taken to achieve 50% of drug dissolution ($t_{50\%}$). % DE is the area under the dissolution curve between two specified time points expressed as a percentage of the area of the rectangle described by 100% dissolution in the same time intervals, which can be calculated using Eq. (II) above. Taking pure indomethacin as the reference, capsules produced a 2-5 fold improvement in % DE at the initial stage (ie the first 5-15 min). The value of $t_{50\%}$ was substantially reduced by capsules (5.0±0.5 min) compared to pure indomethacin (58.8±0.5 min) and o/w emulsion (12±1 min). With the conventional assumption that the rate and extent of drug dissolution directly reflects the concentration of readily absorbable drug in the intestinal lumen, it is proposed that capsules have the potential to enhance the oral absorption process. Thus, capsules attained more than 85% of drug dissolution within 30 min under appropriate sink conditions, hence meeting the FDA criteria for classification as immediate-release dosage forms. It should be emphasised that the surface area of o/w submicron emulsions, spray dried silica and capsules is in good agreement with dissolution profiles (FIG. 8). The dissolution kinetics can be fitted into Peppas model:

$$M_t/M_0 = at^n \quad (III)$$

where $M_0$ is the initial amount of drug in the pharmaceutical dosage form, $M_t$ is the amount of drug at time t and n value is 0.5 for Fick diffusion (ie the Higuchi drug release mechanism is applicable if (i) the initial drug concentration in the system is much higher than the matrix solubility; (ii) perfect sink conditions are maintained; (iii) the diffusivity of the drug is constant and (iv) the swelling of the matrices is negligible). The sink conditions are achieved by ensuring the concentration of the released drug in the release medium reaches no more than 10% of its saturation solubility. Release behavior presented in FIG. 8 can be well fitted into diffusion model with n=0.5 (r=0.99). Higuchi release rate constants were calculated to be 12.4, 23.7 and 43.8 min$^{-1}$ for oil/phospholipid solution, o/w submicron emulsion and capsules, respectively.

BET surface area of the capsules after oil extraction (184 m²/g) and interfacial area of submicron droplets (5.68 m²/g) can be directly correlated to the release kinetic data.

In Vivo Pharmacokinetics

The oral absorption of indomethacin from the aqueous suspension, o/w submicron emulsion and silica lipid hybrid capsules was studied in a fasted rat model and the corresponding pharmacokinetic data is summarised in Table 5.

TABLE 5

Pharmacokinetic data for rats after administration of 1.78 mg/kg indomethacin

| Indomethacin Formulations | PK parameters | | | |
|---|---|---|---|---|
| | $t_{max}$ (min) | $C_{max}$ (µg/ml) | $AUC_{0 \to \infty}$ (min · µg/ml) | F (%) |
| I.V. injection | — | | 66.92 ± 6.74 | — |
| Oral control systems | | | | |
| Aqueous suspension | 2.75 ± 0.65 | 2.48 ± 0.38 | 35.83 ± 1.95 | 53.54 ± 2.91 |
| o/w emulsion | 1.13 ± 0.25 | 3.16 ± 1.03 | 43.22 ± 1.41 | 64.57 ± 2.11 |
| Oral capsules | 1.83 ± 0.29 | 4.17 ± 0.75* | 62.29 ± 3.40* | 93.07 ± 5.09* |

*statistically higher than aqueous suspension and o/w emulsion (p < 0.05)

The indomethacin aqueous suspension gave the lowest bioavailability in fasted rats (53.5%). The pharmacokinetic profile for the o/w submicron emulsion (64.6±2.1%) was not significantly different from that of the aqueous suspension (53.5±2.9%) (Table 5). The capsules demonstrated a significant increase in the fasted state bioavailability (93.1±05.1%) as compared to indomethacin aqueous suspension and o/w emulsion (p<0.05). Statistical analysis showed that capsules resulted in a superior $C_{max}$ compared to the aqueous suspensions and o/w submicron emulsions (p<0.05). It is apparent that differences in the size (submicron emulsion vs. capsules) did not have a pronounced effect on the extent of indomethacin absorption.

Capsules were shown to exhibit a statistically higher $C_{max}$ (4.17±0.75 µg/ml) in comparison to all other tested formulations (p<0.05) (2.48±0.38 µg/ml for aqueous suspension and 3.16±1.03 µg/ml for o/w submicron emulsion). The higher $C_{max}$ and bioavailability provide an opportunity to lower the dose of drugs such as indomethacin that can cause local irritation in the GIT at high doses, hence the incidence of GI bleeding and ulceration would be reduced.

Drug Delivery Mechanism of Capsules

It is well established that the in vitro dissolution rate is not a sufficient parameter for assessment of lipid based formulations. Lipolysis experiments have enhanced the understanding of the changes to solubilisation capacity that might occur on lipid digestion, with a series of colloidal structures, including multilamelar and unilamellar vesicles, mixed micelles and micelles. Recent data (Fatouros et al., 2007) suggest that lipolysis is a dynamic process of exchange between a lamellar phase formed immediately after initiation of lipolysis and hexagonal phase. Further, the formation of liquid crystalline phases is governed by hydrolytic degradation of oil droplets to mono and di glycerides and fatty acids. Moreover, it is suggested that the in vivo performance of lipid-based systems is more dependent on the interaction between formulation lipids and lipid digestion products with the secreted bile contents in the intestinal lumen.

Figure 9:
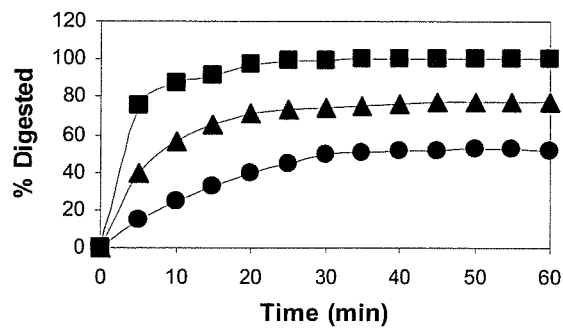
FIG. 9 provides A. Lipid degradation of ■lecithin stabilised capsules; ▲ equivalent o/w submicron emulsions; ● lipid solutions. B. Indomethacin content in the supernatant during lipolysis: black bar lecithin stabilised capsules; grey bar—equivalent o/w submicron emulsions; white bar—lipid solutions.
Figure 9:
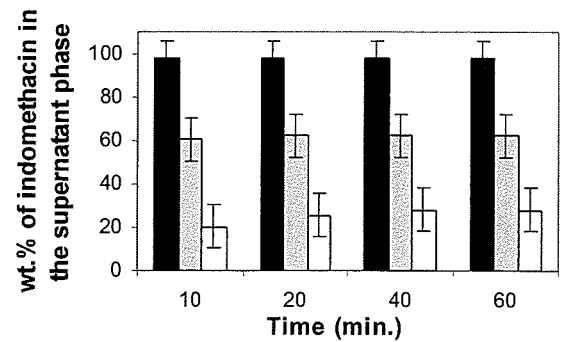

To further explore the mechanisms of capsule drug delivery, in vitro lipolysis was performed in conjunction with drug content analysis. The data suggest that lipolysis rate and extent of lipolysis is much higher for capsules than equivalent submicron droplets or lipid solutions (FIG. 9a). Partial lipolysis of submicron lecithin stabilised droplets and lipid lecithin solutions may be explained by formation of viscous liquid crystalline phases at the droplet surfaces that prevent further lipolysis. Moreover, indomethacin content in supernatant soluble phases is significantly higher for capsules in comparison with o/w submicron droplets and lipid solutions (FIG. 9b). Capsules were imaged after 4 hours of dissolution and 1 hour of lipolysis: it was observed that capsules retained their structural integrity, so it is reasonable to assume silica nanoparticles do not penetrate into enterocites (ie they are considered inert porous structures). Moreover, thermogravimetric lipid content measurements showed that capsules completely lose their lipid content after 10 min of dissolution and lipolysis. This is a confirmation that capsules represent a novel delivery system for poorly soluble anti-inflammatory drugs and that they are not equivalent to simple mixtures of submicron droplets and silica matrices. If this was the case, the lipolytic profile would be the same for submicron droplets and capsules. Based on the presented results, it may be hypothesised that oil and phospholipid are adsorbed within the silica amorphous matrix structure and upon contact with dissolution/digestion medium nanodroplets are released and undergo faster lipolytic degradation than submicron droplets, and hence improved adsorption in vivo.

Conclusion

The capsules exhibit an internal porous matrix structure composed of oil attached to a silica matrix by lipophilic negatively or positively charged surfactants. Surfactant charge has a profound effect on capsule formation, as capsules can be fabricated with ten times less nanoparticles when a charge neutralisation mechanism is operative. The model drug indomethacin exhibited excellent storage stability under accelerated storage conditions of 6 months. In vivo studies in orally dosed rats confirmed statistically higher (p<0.05) bioavailability and $C_{max}$ in comparison with o/w submicron emulsions and an aqueous drug suspension. Enhanced drug release due to the high surface area of amorphous silica matrices and enhanced lipolysis are the principal drug delivery mechanisms.

Example 3

Bioavailability of Nanoparticle-Stabilised Indomethacin Capsule Formulation

Materials and Methods

Preparation of Capsules

Nanoparticle-stabilised indomethacin capsule formulations according to Table 6 were prepared as follows:

Spray-Dried Formulations

Oleylamine was dissolved in the oil phase (caprylic capric triglyceride), silica nanoparticle powder was added (formulation 2, 3, 5, and 7) and the mixture sonicated. Indomethacin was added with swirling and ultrasonic treatment. MilliQ water was added before being homogenised in a high pressure homogeniser (Avestin EmulsiFlex-C50 High Pressure Homogenizer) for 5 cycles under pressure 5 mbar. After the emulsion was homogenised, 250 ml silica solution (2.5 g silica dispersed in 100 ml MilliQ-RG purified water) was added and shaken for 2 hours in order to mix uniformly. The capsule dry powder was obtained by spray drying (Buchi 190 Mini Spray Dryer).

Filtered and Air-Dried Formulations

Samples were prepared as for the spray-dried formulations, but in this case the capsule dry powder was obtained by filtering through Millipore filter and air drying.

TABLE 6

Formulation compositions

| Batch | Oil (g) | Indomethacin (g) | Oleylamine (g) | Silica (g) | Preparation method |
|---|---|---|---|---|---|
| 1 | 10 | 0.025 | 1 | | Spray dry |
| 2 | 10 | 0.025 | 1 | 0.5 | Spray dry |
| 1a | 10 | 0.025 | 1 | | Filter and air dry |
| 2a | 10 | 0.025 | 1 | 0.5 | Filter and air dry |
| 3 | 10 | 0.2 | 1 | 0.5 | Spray dry |
| 3a | 10 | 0.2 | 1 | 0.5 | Filter and air dry |
| 4 | 10 | 1 | 1 | | Spray dry |
| 5 | 10 | 1 | 1 | 1 | Spray dry |
| 4a | 10 | 1 | 1 | | Filter and air dry |
| 5a | 10 | 1 | 1 | 1 | Filter and air dry |

Detection of Capsule Size and Zeta Potential Upon Re-Dispersion

The capsule size and Zeta potential for the nanoparticle-stabilised capsule formulations and control indomethacin emulsions, upon redispersion in simulated body fluid, was determined as follows: Emulsions were diluted before measurements. 100 mg of nanoparticle-stabilised indomethacin capsule powder was weighed into a clean and dry vial. Preparative solution (pH 7.2 phosphate buffer solution, ~10 mL or pH 1.2 buffer solution, ~10 mL) was added. The suspension was shaken for 4 hours and then left standing for 2 hours before it was determined. The measurement of size was divided into four sections. Two buffer solutions (pH 7.2 phosphate buffer solution and pH 1.2 buffer solution) were chosen. Some of the suspension solution was filtered through a 0.8 μm filter before analysis. The measurement of Zeta potential was divided into two sections. Two buffer solutions (pH 7.2 phosphate buffer solution and pH 1.2 buffer solution) were chosen. The Zeta potential of the suspension was then determined.

Determination of Indomethacin Drug Loading Level
The Extraction Recovery of Sample 0.025 g of oleylamine and 0.0125 g of silica nanoparticles were weighed into a clean and dry 100 ml bottle. 0.25 g oil (caprylic capric triglyceride) was added. 0.005 g of indomethacin was accurately weighed and added. The solid was dissolved with swirling and ultrasonic treatment. 20 g of acetonitrile was accurately weighed and added. The solution was ultrasonically processed for 30 mins. 30 g of pH 7.2 phosphate buffer was accurately weighed and added. The solution was ultrasonically processed for 30 mins. 50 g of acetonitrile was accurately weighed and added. The solution was ultrasonically processed for 4 hours. 2 ml of this solution was withdrawn and centrifuged at 12000 g for 10 min. The suspension was separated and the supernatant injected HPLC for analysis.

Detection of Indomethacin Drug Loading Level 0.005 g of nanoparticle-stabilised capsule formulation was accurately weighed into a clean and dry vial. 2 g of acetonitrile was accurately weighed and added. The solid was dispersed with swirling and ultrasonic treatment. The solution was ultrasonically processed for 30 mins. 3 g of pH 7.2 phosphate buffer was accurately weighed and added. The solution was ultrasonically processed for 30 mins. 5 g of acetonitrile was accurately weighed and added. The solution was ultrasonically processed for 4 hours. 2 mL of this solution was withdrawn and centrifuged at 12000 g for 10 min. The suspension was separated and 20-50 μL of the supernatant injected for analysis. A SHIMADZU HPLC system with SCL-10A system controller, LC-10AT pump, SIL-10A auto sample and injector and SPD-10A UV-VIS detector was employed. Column: Alltech Lichrospher 100 RP-18 (4.6 mm×250 mm 5 μm). Software: SHIMADZU CLASS-VP (data acquisition and analysis). Flow rate: 1.0 ml/min. Observe: 320 nm for 10 minutes. Mobile phase: MilliQ-RG purified water (35 ml) was added to Acetonitrile (65 ml). Acetic acid (0.1 ml) was added to each 100 ml of solution. The mobile phase solution was mixed and then degassed.

Differential Scanning Calorimetry

The sample sealed in the aluminium crimp cell was heated at a speed of 5° C./min from 30° C. to 200° C. in an atmosphere of nitrogen. Peak transition onset temperature was determined by the analyser. The peak transition onset temperatures of pure indomethacin, different indomethacin loaded levels of nanoparticle-stabilised capsule powder samples and a blank of capsule excipient powder were compared.

Measurement of Indomethacin Dissolution Rate from Nanoparticle-Stabilised Capsules
(Reference—USP 28 Drug Dissolution (Method B))

Apparatus: SRII 6-Flask Dissolution Test Station, Hanson Research, Chatsworth, Calif., United States of America.

Dissolution of nanoparticle-stabilised indomethacin capsules was performed in a covered vessel with a paddle assembly at 75 rpm at 37±0.5° C. Capsules were placed in an individual vessel which was immersed in 900 ml of pH 7.2 phosphate buffer for 6 hours. An aliquot of 2 ml was withdrawn for an analysis after 5 min, 10 min, 15 min, 30 min, 45 min, 60 min, 90 min, 120 min, 150 min, 180 min, 210 min, and 240 min. Immediately, the amount withdrawn was replaced with fresh pH 7.2 phosphate buffer solution. Each sample was filtered with 0.8 μm filter before it was assayed by HPLC with UV detection at 320 nm.

Rat Bioavailability and Pharmacokinetics

Groups of 5 male Sprague-Dawley rats weighing 320±20 g were used for an absorption study. One group was dosed intravenously with 1.78 mg/kg indomethacin in PEG 400/saline (2:1 v/v) solution, while the other groups were administered orally with one of the following formulations at the same dose by oral gavage: indomethacin aqueous suspension, indomethacin o/w liquid lecithin based submicron emulsion and indomethacin capsules according to the present invention. Pure indomethacin powder was suspended in 0.25% (w/v) sodium carboxymethylcellulose, while capsules were re-dispersed in Milli-Q water at a suitable concentration. The cannulated rats were fasted overnight (14±1 h) prior to each oral dosing and were given access to food 4 h post-dose, with water was accessible at all time. Blood samples (0.2 ml) were collected from the jugular vein at designated time intervals 0.083, 0.25, 0.5, 1, 1.5, 2, 2.5, 3, 4, 6, 8, 24 h post-dose, and the cannula was flushed with an equal volume of heparinised normal saline (50 units/5 ml) to prevent blood clotting. Blood samples (about 200 μL) were collected in heparinised 1.5 ml polythene tubes immediately at different times after dosing, and centrifuged at 800 rpm for 10 min at 4° C. Ten aliquot of 100 μL of plasma sample, 10 μL of acemetacin as an internal standard (IS, 20 μg/ml) was mixed for 30 s. After addition of 200 μL of acetonitrile with 0.1% acetic acid, the mixture was vortex-mixed for 1 min and centrifuged at 10000 g for 10 min to remove proteins. Indomethacin content in the supernatant was determined by HPLC. The chromatographic separation was performed using an Alltech Lichrospher 100 RP-18 (4.6 mm×250 mm, 5 μm) analytical column. The mobile phase consisted of a mixture of 0.1% (v/v) acetic acid in methanol:acetonitrile:distilled water (60:20:20 v/v), ultrasonically degassed prior to use. The mobile phase was delivered at a flow-rate of 1.0 ml/min, the detection wavelength was 320 nm, the attenuation was 0.001 and the injection volume was 20 μL. The pharmacokinetic parameters were determined using the PC software, WinNonlin® Standard Edition Version 4.1 (Pharsight Corp.), employing a non-compartmental model. The maximum plasma concentration (Cmax) and the time at which Cmax is reached (tmax) were obtained from the individual plasma concentration-time curves. The area under the plasma concentration-time curve from time zero to infinity (AUC0→∞) was calculated using the linear trapezoidal rule. The values of AUC0→∞ obtained were used to estimate the absolute bioavailability (F) according to Eq. (1) above.

In Vitro Digestion Experiments

In vitro digestion experiments were performed: 0.1 g of lipid (indomethacin solution in miglyol containing 0.6% lecithin, equivalent submicron emulsion and microcapsule) was dispersed in 20 mL of digestion buffer (50 mM TRIS maleate, 150 mM NaCl, 5 mM $CaCl_2 \times 2H_2O$, pH 7.5) containing 5 mM NaTDC and 1.25 mM phosphatidyl choline (PC) (conditions broadly representative of fasted state intestinal conditions). Experiments were performed at 37° C. in a stirred and thermostated glass vessel and were initiated by the addition of 3 mL of pancreatin extract containing 40000 tributyrin units (TBU) of pancreatic lipase (final lipase concentration of 1000 TBU per mL digest). Lipolysis was followed over 60 min using a pH-stat titration unit (Radiometer, Copenhagen, Denmark), which maintained the pH at 7.5. The fatty acids produced on lipolysis were titrated with 0.6 M NaOH. Aliquots (1.4 mL) were taken from the digestion medium at 5, 10, 15, 30, 45 and 60 min and a lipolysis inhibitor (0.5 M 4-BPB in methanol, 9 μL/mL digestion medium) immediately added to each sample to prevent further lipolysis. Samples were subsequently ultracentrifuged for 30 min at 37° C. and 334000 g (Optima XL-100K centrifuge, SW-60 rotor, Beckman, Palo Alto, Calif., United States of America) in order to separate the digests into an aqueous phase and a pellet phase. Samples obtained from each separated phase were assayed for indomethacin content by HPLC. Blank digestion experiments were also performed to account for the fatty acids produced on digestion of the lecithin present in the digestion media. Lecithin samples typically contained small quantities of glycerides (1% w/w triglyceride; 6% w/w diglyceride; <1% w/w fatty acids) and PC which is hydrolysed by phospholipase $A_2$ (present in pancreatin) to produce fatty acids and lyso-PC. Blank digestion experiments were therefore performed in the same manner as that described above, but in the absence of the added formulation. The digestion data obtained for the experimental formulations were subsequently corrected for background fatty acid production (ie fatty acids derived from the lecithin present in the digestion media) by substraction of the fatty acids produced during blank digestion experiments.

Results and Discussion

Detection of Capsule Size and Zeta Potential Upon Re-Dispersion

The results of the detection of the capsule particle size and Zeta potential for nanoparticle-stabilised indomethacin capsules is shown in Table 7. The results demonstrated that the capsules show good physical stability.

TABLE 7

Particle size for spray-dried nanoparticle-stabilised indomethacin capsules

| Buffer solution | Zeta Potential (mv) | Particle Size (nm) | |
|---|---|---|---|
| | | Before filtering | After filtering |
| pH 1.2 Buffer solution | 45.2 | 335.6 | 293.2 |
| pH 7.2 Buffer solution | −16.2 | 3713 | 1616 |
| pH 1.2 Buffer solution | 45.2 | 20 | 293.2 |
| pH 7.2 Buffer solution | −16.2 | 20 | 1616 |

Determination of Indomethacin Drug Loading Level

The results of the investigation of drug loading levels showed that the extraction recoveries reached 100±5%. Different indomethacin loading levels have been prepared as shown in Table 8.

TABLE 8

| Batch | Drug loading level | and entrapment efficiency(%) |
|---|---|---|
| 1 | 0.05 | 55 |
| 2 | 0.06 | 60 |
| 1a | 0.08 | 98 |
| 2a | 0.09 | 100 |
| 3 | 0.9 | 69.12 |
| 3a | 1.3 | 100 |
| 4 | 5.16 | 81.6 |
| 5 | 5.34 | 82.9 |
| 4a | 6.15 | 96 |
| 5a | 6.18 | 96 |

Differential Scanning Calorimetry

Differential scanning calorimetry (DSC) thermograms were prepared for pure and encapsulated indomethacin. It was observed from the thermograms that the crystalline drug peak disappeared with the nanoparticle-stabilised capsules and is absent during storage under accelerated conditions. The DSC of pure indomethacin showed a sharpened endothermal peak with an onset melting point of 159.41° C. This typical peak of indomethacin was not observed in any of the DSC curves for the nanoparticle-stabilised indomethacin capsules.

Figure 10:
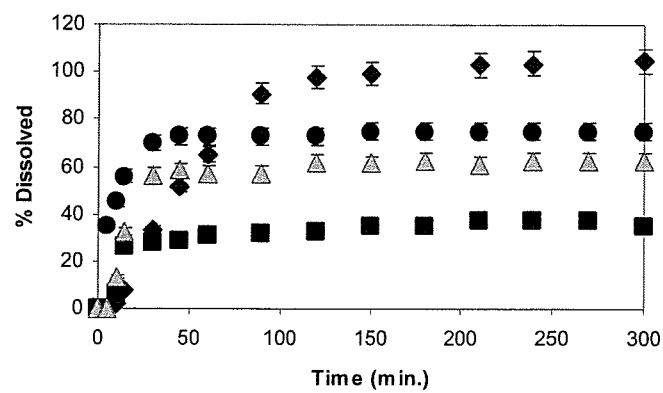
FIG. 10 provides graphical results showing the dissolution profiles of indomethacin (3.3 mg) from nanoparticle-stabilised capsules with different drug loading levels and pure indomethacin drug. A. Spray-dried formulations: ◆ pure indomethacin, ■ indomethacin (0.06%), ▲ indomethacin (0.91%), and ● indomethacin (5.16%). B. Filtered and air-dried formulations: ◆ pure indomethacin, ■ indomethacin (0.08%), ▲ indomethacin (1.3%), and ● indomethacin (6.15%)
Figure 10:
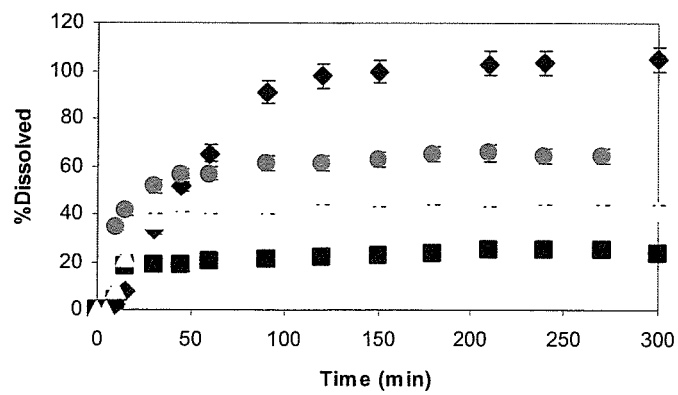

Measurement of Indomethacin Dissolution Rate from Nanoparticle-Stabilised Capsules Capsules with different indomethacin loading levels were assessed in dissolution studies, the results of which are shown in FIG. 10. It is considered that indomethacin release from the nanoparticle-stabilised capsules was incomplete due to the formation of indomethacin-oleylamine electrostatic bonding.

Rat Bioavailability and Pharmacokinetics

Figure 11:
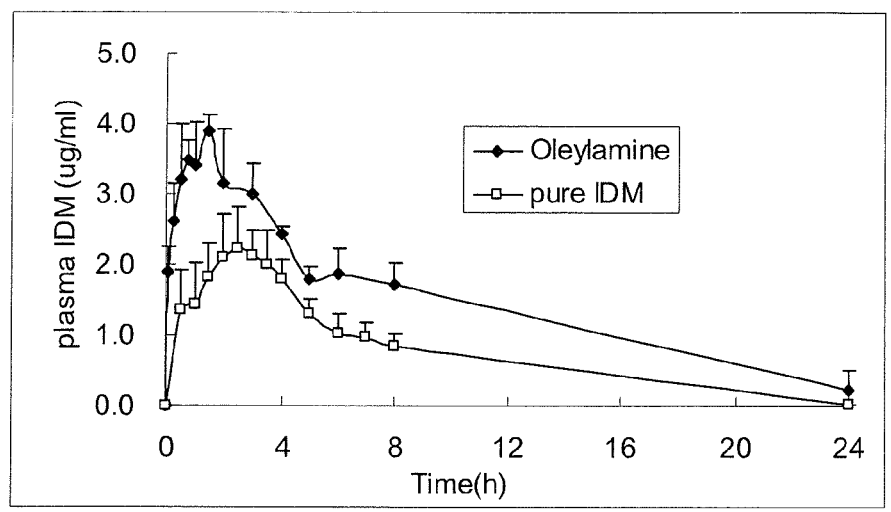
FIG. 11 provides a graph of the time course of indomethicin (IDM) in rat plasma after gavage (1.78 mg/kg): (□) pure indomethacin, and (◆) nanoparticle-stabilised indomethacin capsules (oleylamine)

The time course of indomethacin (IDM) in rat plasma after gavage (1.78 mg/kg) is shown in FIG. 11 (n=4); and the pharmacokinetic parameters of indomethacing after i.v. and o.p. administration of nanoparticle-stabilised capsules and pure indomethacin are given in Table 9. Despite incomplete in vitro release, the bioavailability determined in rat is very high (88.5-100%) and significantly greater than that which has been observed in the commercial indomethacin formulation, Indocid.

TABLE 9

Pharmacokinetic parameters

| Parameter | I.V. | pure IDM | Oleylamine caps. Loading 0.06% |
|---|---|---|---|
| HL_Lambda_z (h) | 3.40 ± 0.08 | 2.79 ± 0.31 | 3.95 ± 0.59 |
| Tmax (h) | | 2.75 ± 0.65 | 1.25 ± 0.61 |
| Cmax (ug/ml) | | 2.48 ± 0.38 | 3.70 ± 0.48 |
| AUCINF_D_pred h*ug/ml/mg | 66.92 ± 6.74 | 35.83 ± 1.95 | 59.22 ± 2.98 |
| F(%) | | 53.54 ± 2.91 | 88.50 ± 4.46 |

In Vitro Digestion Experiments

Figure 12:
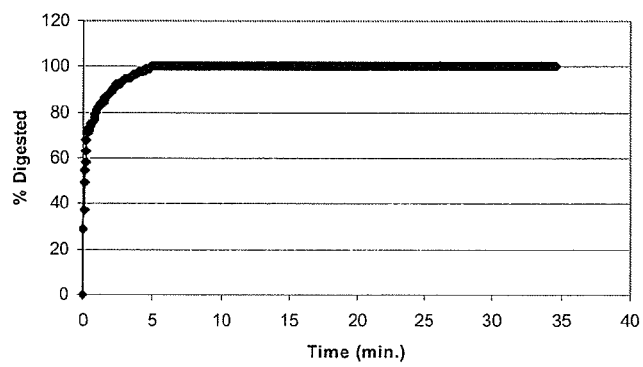
FIG. 12 provides a typical lipolysis curve obtained with a spray-dried formulation of nanoparticle-stabilised indomethacin capsules.
Figure 13:
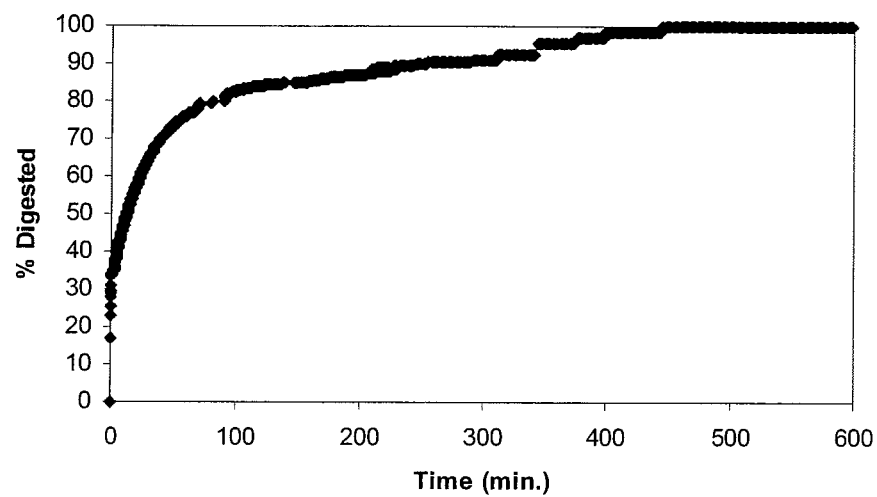
FIG. 13 provides A. a lipolysis curve for a filtered and air-dried formulation of nanoparticle-stabilised indomethacin capsules, and B. a bar graph showing the percentage of indomethacin dissolved over time.
Figure 13:
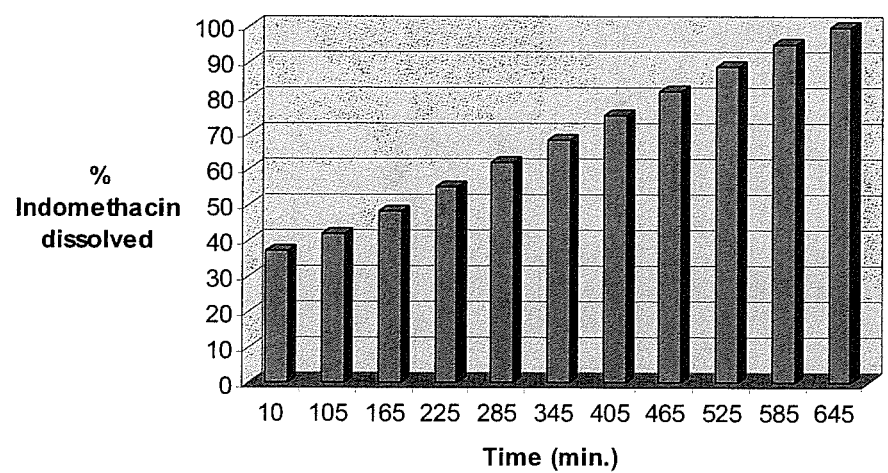

The results of the in vitro digestion experiments are shown in FIGS. 12 and 13. For spray-dried nanoparticle-stabilised indomethacin capsules, the typical lipolysis curves (see, for example, FIG. 12) showed that 70-75% of the indomethacin was detected after 5 min. with 95-100% digested after 15 min. For filtered and air-dried nanoparticle-stabilised indomethacin capsules, the lipolysis curves (see, for Example, FIG. 13 from Sample 5a), lipolysis was controlled over 10 hours with subsequent drug solubilisation.

Although a preferred embodiment of the apparatus of the present invention has been described in the foregoing detailed description, it will be understood that the invention is not limited to the embodiment disclosed, but is capable of numerous rearrangements, modifications and substitutions without departing from the scope of the invention. Modifications and variations such as would be apparent to persons skilled in the art are deemed to be within the scope of the present invention. For example, although the invention is generally discussed with reference to emulsion droplets, the techniques discussed can generally be applied to liposomes, other vesicle systems and other similar vehicles.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES

Boyd, B. J., Khoo, S.-M., Whittaker, D. V., Davey, G., & Porter, C. J. H. (2007). A lipid-based liquid crystalline matrix that provides sustained release and enhanced oral bioavailability for a model poorly water soluble drug in rats. *Int. J. Pharm.* 340(1-2):52-60.

Eskandar, N. G., Simovic, S., & Prestidge, C. A. (2007). Synergistic effect of silica nanoparticles and charged surfactants in the formation and stability of submicron oil-in-water emulsions, *Phys. Chem. Ch. Ph.* 9(48):6426-6434.

Fatouros, D. G., Deen, G. R., Arleth, L., Bergenstahl, B., Nielsen, Flemming S., Pedersen, J. Skov, & Mullertz, A. 2007. Structural Development of Self Nano Emulsifying Drug Delivery Systems (SNEDDS) During In Vitro Lipid Digestion Monitored by Small-angle X-ray Scattering. *Pharm. Res.* 24(10):1844-1853.

Fischer, S. M., Lo, H. H., Gordon, G. B., Seibert, K., Kelloff, G., Lubet, R. A., & Conti, C. J. (1999). Chemopreventative activity of celecoxib, a specific cyclooxygenase inhibitor, and indomethacin against ultraviolet light-induced skin carcinogenesis. *Molecular Carcinogenesis* 25(4): 231-240.

Fulton, A. M. (1984). In vivo effects of indomethacin on the growth of murine mammary tumors. *Cancer Research* 44(6): 2416-2420.

Harris, R. E., Alshafie, G. A., Abou-Issa, H., & Seibert, K. (2000). Chemoprevention of breast cancer in rats by celecoxib, a cyclooxygenase 2 inhibitor. *Cancer Research* 60(8):2101-2103.

Humberstone, A. J., & Charman, W. N. (1997). Lipid-based vehicles for the oral delivery of poorly water soluble drugs. *Adv. Drug Deliv. Rev.* 25(1):103-128.

Kawamori, T., El-Bayoumy, K., Ji, B. Y., Rodriguez, J. G., Rao, C. V., & Reddy, B. S. (1998). Evaluation of benzyl selenocyanate glutathione conjugate for potential chemopreventive properties in colon carcinogenesis. *International Journal of Oncology* 13(1):29-34.

Kujubu, D. A., Fletcher, B. S., Varnum, B. C., Lim, R. W., & Herschman, H. R. (1991). TIS10, a phorbol ester tumor promoter-inducible mRNA from Swiss 3T3 celecoxibls, encodes a novel prostaglandin synthase/cyclooxygenase homologue. *Journal of Biological Chemistry* 266(20): 12866-12872.

Masferrer, J. L., Seibert, K., Zweifel, B., & Needleman, P. (1992). Endogenous glucocorticoids regulate an inducible cyclooxygenase enzyme. *Proceedings of the National Academy of Sciences of the United States of America* 89(9): 3917-3921.

Narisawa, T., Satoh, M., Sano, M., & Takahashi, T. (1983). Inhibition of initiation and promotion of N-methylnitrosourea induced colon carcinogenesis in rats by nonsteroidal anti-inflammatory agent indomethacin. *Carcinogenesis* 4(10):1225-1227.

Pedersen, G. P., Faldt, P., Bergenstahl, B., & Kristensen, H. G. (1998) Solid state characterisation of a dry emulsion: a potential drug delivery system. *Int. J. Pharm.* 171(2):257-270.

Pentland, A. P., Schoggins, W., Scott, G. A., Khan, K. N. M., & Han, R. (1999). Reduction of UV-induced skin tumors in hairless mice by selective COX-2 inhibition. *Carcinogenesis* 20(10):1939-1944.

Reddy, B. S., Rao, C. V., Rivenson, A., & Kelloff, G. (1993). Inhibitory effect of aspirin on azoxymethane-induced colon carcinogenesis in F344 rats. *Carcinogenesis* 14(8): 1493-1497.

Seibert, K., Zhang, Y., Leahy, K., Hauser, S., Masferrer, J., Perkins, W., Lee, L., & Isakson, P. (1994). Pharmacological and biochemical demonstration of the role of cyclooxygenase 2 in inflammation and pain. *Proceedings of the National Academy of Sciences of the United States of America* 91(25):12013-12017.

Simovic, S., & Prestidge, C. A. (2007). Nanoparticle layers controlling drug release from emulsions, Eur. *J. Pharm. Biopharm.* 67(1):39-47.

Sood S., Shiff S. J., Yang C. S., & Chen X. (2005). Selection of topically applied non-steroidal anti-inflammatory drugs for oral cancer chemoprevention. *Oral Oncology* 41(6): 562-567.

Takeuchi, H., Nagira, S., Yamamoto, H., & Kawashima, Y. (2005). Solid dispersion particles of amorphous indomethacin with fine porous silica particles by using spray-drying method. *Int. J. Pharm.* 293(1-2):155-164.

Xie, W. L., Chipman, J. G., Robertson, D. L., Erikson, R. L., & Simmons, D. L. (1991). Expression of a mitogen-responsive gene encoding prostaglandin synthase is regulated by mRNA splicing. *Proceedings of the National Academy of Sciences of the United States of America* 88(7): 2692-2696.

Zarghi, A., Shafaati, A., Foroutan, S. M., & Khoddam, A. (2006). Simple and rapid high-performance liquid chromatographic method for determination of celecoxib in plasma using UV detection: application in pharmacokinetic studies, *J. Chromatogr.* B 835(1-2):100-104.

The invention claimed is:

1. A nanoparticle-stabilised capsule formulation comprising
    a discontinuous phase comprising droplets comprising:
        an oil-based or lipidic medium carrier selected from the group consisting of:
            triglyceride oils (medium or long-chained), soyabean oil, sunflower oil and almond oil,
        an anti-inflammatory agent selected from the group consisting of celecoxib and indomethacin, and
        an emulsifier selected from the group consisting of lecithin and oleylamine,
    wherein the anti-inflammatory agent is present in the discontinuous phase at a concentration in the range of 0.01 to 10 wt. %,
    wherein said droplets are stabilised with nanoparticles coated on the surface of the droplets, and
    wherein the nanoparticles are selected from the group consisting of silica nanoparticles, titania nanoparticles and latex nanoparticles.

2. The formulation of claim 1, wherein nanoparticles are also dispersed within said carrier.

3. The formulation of claim 1, wherein the said droplets are coated with at least one layer of nanoparticles.

4. The formulation of claim 1, wherein the anti-inflammatory agent is indomethacin.

5. The formulation of claim 1, wherein the anti-inflammatory agent is celecoxib.

6. The formulation of claim 1, wherein the formulation is for oral administration to a subject.

7. The formulation of claim 1, wherein the anti-inflammatory agent is present in an amount that is greater than its solubility limit in the discontinuous phase.

8. The formulation of claim 7, wherein the anti-inflammatory agent is present in an amount that is at least about 110% of its solubility limit in the discontinuous phase.

9. The formulation of claim 8, wherein the anti-inflammatory agent is present in an amount that is at least about 120% of its solubility limit in the discontinuous phase.

10. The formulation of claim 9, wherein the nanoparticles are silica.

11. The formulation of claim 1, wherein the formulation contains no other surfactants.

12. The formulation of claim 1, wherein the nanoparticles have an average diameter of 2 nm to 2000 nm.

13. The formulation of claim 12, wherein the nanoparticles have an average diameter of 5 nm to 80 nm.

14. The formulation of claim 13, wherein the nanoparticles have an average diameter of about 7 nm.

15. The formulation of claim 1, wherein the ratio of nanoparticle size to capsule size of the encapsulated droplets does not exceed 1:15.

16. A dried nanoparticle-stabilised capsule formulation comprising:
    an anti-inflammatory agent selected from the group consisting of celecoxib and indomethacin,
    said formulation comprising capsules comprising a porous matrix of:
        said anti-inflammatory agent,
        an oil-based or lipidic medium suitable carrier selected from the group consisting of triglyceride oils (medium or long-chained), soyabean oil, sunflower oil and almond oil,
        nanoparticles selected from the group consisting of silica nanoparticles, titania nanoparticles and latex nanoparticles and,
        an emulsifier selected from the group consisting of lecithin and oleylamine,
    wherein said capsules have a diameter in the range of 1 to 5 μm
    and an average pore size within the matrix of 25 to 500 nm,
    and wherein said capsules are dispersible into droplets of said carrier, comprising the anti-inflammatory agent, that are stabilised with nanoparticles coated on the surface of the droplets.

17. The formulation of claim 16, wherein the formulation has been dried by spray drying, freeze drying, vacuum drying, or phase coacervation (filtration).

18. The formulation of claim 16, wherein the formulation has been spray-dried.

19. The formulation of claim 16, wherein said capsules are capable of being dispersed into droplets of said carrier comprising said anti-inflammatory agent stabilised with nanoparticles coated on the surface of the droplets and dispersed within said carrier.

20. The formulation of claim 16, wherein the anti-inflammatory agent is indomethacin.

21. The formulation of claim 16, wherein the anti-inflammatory agent is celecoxib.

22. The formulation of claim 16, wherein the formulation is for oral (p.o.) administration to a subject.

23. A method for administering an anti-inflammatory agent to a subject, wherein said method comprises administering to said subject a formulation according to claim 16.

24. The method of claim 23, wherein the subject is suffering from pain and/or inflammation, or cancer.

25. The formulation of claim 16, wherein the emulsifier is lecithin and the average pore diameter is in the range of 100 to 500 nm.

26. The formulation of claim 25, wherein the lecithin conveys a negative charge to the droplets.

27. The formulation of claim 16, wherein the emulsifier is oleylamine, wherein the oleylamine conveys a positive charge to the droplets, and wherein the porous matrix contains a higher proportion of pores with a diameter of 25-200 nm than a matrix comprising lecithin.

28. A method for administering an anti-inflammatory agent to a subject, wherein said method comprises administering to said subject a formulation according to claim 1.

29. The method of claim 28, wherein the subject is suffering from pain and/or inflammation, or cancer.

30. A method for producing a formulation of an anti-inflammatory agent,
    wherein said anti-inflammatory agent is selected from the group consisting of celecoxib and indomethacin,
    wherein said method comprises preparing a nanoparticle-stabilised preparation comprising a discontinuous phase comprising droplets comprising:
  an oil-based or lipidic medium carrier selected from the group consisting of triglyceride oils (medium or long-chained), soyabean oil, sunflower oil and almond oil, said anti-inflammatory agent, and
  an emulsifier selected from the group consisting of lecithin and oleylamine,
wherein the anti-inflammatory agent is present in the discontinuous phase at a concentration in the range of 0.01 to 10 wt. %,
wherein said droplets are stabilised with nanoparticles coated on the surface of the droplets, and
wherein the nanoparticles are selected from the group selected from the group consisting of silica nanoparticles, titania nanoparticles and latex nanoparticles.

31. The method of claim 30, wherein in preparing said nanoparticle-stabilised preparation, nanoparticles are also dispersed within said carrier.

32. The method of claim 30, wherein in preparing said nanoparticle-stabilised preparation, the droplets are coated with at least one layer of nanoparticles.

33. The method of claim 30, wherein the anti-inflammatory agent is indomethacin.

34. The method of claim 30, wherein the anti-inflammatory agent is celecoxib.

35. The method of claim 30, wherein the method further comprises drying the nanoparticle-stabilised preparation.

36. The method of claim 35, wherein the nanoparticle-stabilised preparation is dried by spray drying, freeze drying, vacuum drying, or phase coacervation (filtration).

37. The method of claim 35, wherein the nanoparticle-stabilised preparation is dried by spray drying.

38. A dried nanoparticle-stabilised formulation produced in accordance with the method of claim 35.

39. A dried nanoparticle-stabilised formulation produced in accordance with the method of claim 37.

40. The method of claim 30, wherein the nanoparticle-stabilised preparation is for oral (p.o.) administration to a subject.

* * * * *